US012616760B2

(12) United States Patent
Rahimipour et al.

(10) Patent No.: US 12,616,760 B2
(45) Date of Patent: May 5, 2026

(54) SYNTHETIC CYCLIC PEPTIDE MIMETICS

(71) Applicants: BAR ILAN UNIVERSITY, Ramat Gan (IL); UNIVERSITÉ DE MONTRÉAL, Montréal (CA); SOCIETE DE COMMERCIALISATION DES PRODUITS DE LA RECHERCHE APPLIQUEE SOCPRA SCI, Sherbrooke (CA)

(72) Inventors: Shai Rahimipour, Ramat Gan (IL); Maram Habashi, Ramat Gan (IL); Michal Richman, Ramat Gan (IL); William Lubell, Québec (CA); Pradeep Chauhan, Montréal (CA); Suresh Vutla, Montréal (CA); Ramesh Chingle, Frederick, MD (US); Samia Ait-Mohand, Sherbrooke (CA); Veronique Dumulon-Perreault, Sherbrooke (CA); Brigitte Guerin, Westbury (CA)

(73) Assignees: BAR ILAN UNIVERSITY, Ramat Gan (IL); UNIVERSITÉ DE MONTRÉAL, Montréal (CA); SOCIÉTÉ DE COMMERCIALISATION DES PRODUITS DE LA RECHERCHE APPLIQUÉE SOCPRA SCIENCES SANTÉ ET HUMAINES S.E.C., Sherbrooke (CA)

( * ) Notice: Subject to any disclaimer, the term of this patent is extended or adjusted under 35 U.S.C. 154(b) by 558 days.

(21) Appl. No.: 18/044,998

(22) PCT Filed: Sep. 13, 2021

(86) PCT No.: PCT/IL2021/051106
§ 371 (c)(1),
(2) Date: Mar. 13, 2023

(87) PCT Pub. No.: WO2022/054062
PCT Pub. Date: Mar. 17, 2022

(65) Prior Publication Data

US 2024/0316225 A1 Sep. 26, 2024

Related U.S. Application Data

(60) Provisional application No. 63/077,627, filed on Sep. 13, 2020.

(51) Int. Cl.
*A61K 51/08* (2006.01)
*A61K 49/12* (2006.01)
(Continued)

(52) U.S. Cl.
CPC .......... *A61K 51/088* (2013.01); *A61K 49/126* (2013.01); *C07K 7/64* (2013.01);
(Continued)

(58) Field of Classification Search
CPC ............................ A61K 55/088; A61K 49/126
See application file for complete search history.

(56) References Cited

U.S. PATENT DOCUMENTS 9,504,759 B2 11/2016 Rahimipour
2017/0088585 A1 3/2017 Rahimipour

OTHER PUBLICATIONS

Vutla, Suresh, "Azacyclopeptide synthesis and their neuroprotective activity against Abeta toxicity", Retrieved from the Internet: https://papyrus.bib.umontreal.ca/xmlui/handle/1866/25035, Mar. 13, 2019 (Mar. 13, 2019).

(Continued)

*Primary Examiner* — Benjamin J Packard
(74) *Attorney, Agent, or Firm* — JMB Davis Ben-David

(57) ABSTRACT

Described herein are synthetic cyclic peptide mimetics comprising alternating D-amino acids and L-amino acids and
(Continued)

amino acid derivatives, such as aza-amino acids and aza-sulfuryl-amino acids. Optionally, the cyclic peptide mimetics may be conjugated to another agent via a linker to form cyclic peptide mimetic conjugates. The cyclic peptide mimetics described herein may be used as diagnostic or therapeutic agents for diagnosis or treatment of amyloidogenic diseases.

18 Claims, 11 Drawing Sheets
(4 of 11 Drawing Sheet(s) Filed in Color)

(51) Int. Cl.
*C07K 7/64* (2006.01)
*A61K 38/00* (2006.01)

(52) U.S. Cl.
CPC .......... *A61K 38/00* (2013.01); *A61K 2121/00* (2013.01); *A61K 2123/00* (2013.01)

(56) References Cited

OTHER PUBLICATIONS

Merlino, F. et al., "Synthesis of N-Methyl and Azasulfuryl Urotensin-II (4-11) Derivatives", Proceedings of the 24th American Peptide Symposium, American Peptide Society, Jan. 31, 2015 (Jan. 31, 2015).

Sagittal
Sagittal
Sagittal
Coronal
Transaxial
Coronal
Transaxial
Coronal
Transaxial
VOIs
1 2 3 4 5 6 7 8 9 10 11 12 13 14
0.3
0.6%
0.8
ID/g Brain tissue
3.0%
0.7
1.6%

Scheme 1: Synthesis of Carbazates 22-26:

Scheme 2. Synthesis of Azacyclopeptides by On-Resin Cyclization Method

Scheme 3. Synthesis of Azacyclopeptides by Cyclization in Solution

Scheme 4. Synthesis of Aza-triazole-3-alanine Cyclopeptide 13 using CuAAC Reaction.

(14)

(13)

Scheme 5. Synthesis of 1-NOTA and NOTA-Azacyclopeptide Conjugate 40

Compound 1

1-NOTA (19)

(40)

Scheme 6. Synthesis of NOTA(tBu)2CO2H (42) and NOTA-azacyclopeptide conjugate 43

Scheme 7. Synthesis of azasulfuryl tripeptide 51

51

Scheme 8. Solid-phase synthesis of compound 55

SYNTHETIC CYCLIC PEPTIDE MIMETICS

CROSS REFERENCE TO RELATED APPLICATIONS

This is the US National Stage of International Patent Application No. PCT/IL2021/051106 filed Sep. 13, 2021, and benefit is claimed to U.S. Provisional Patent Application No. 63/077,627 filed Sep. 13, 2020; the contents of which is incorporated by reference herein in its entirety.

FIELD

Embodiments relate to synthetic cyclic peptide mimetics and their uses for treatment or diagnosis of disease.

BACKGROUND

Amyloidogenic diseases are characterized by the aggregation of normally soluble proteins into insoluble fibrils in intracellular and extracellular spaces. The amyloid fibrils are usually composed of cross β-sheet structures, which are resistant to metabolic degradation. Amyloidogenic diseases are progressive disorders associated with ageing, morbidity, and high mortality rates. Approximately 50 different peptides and proteins are implicated in amyloid diseases: e.g., amyloid-β (Aβ) in Alzheimer's disease (AD), α-synuclein (α-syn) in Parkinson's disease (PD), Huntingtin protein in Huntington's disease (HD) and amylin in type II diabetes.

Amyloidogenic protein fibrils share typically common structural and biochemical properties irrespective of sequence and chain length. Their similar β-sheet structure features a characteristic cross β-conformation, which can cross-interact and cross-seed with different amyloids in vitro and in vivo to form homogeneous or heterogeneous amyloidogenic protein aggregates. Amyloid proteins share also common functional activities and interact similarly with a variety of membranes to generate channels and pores leading to cellular toxicity.

SUMMARY

Described herein are synthetic cyclic peptide mimetics comprising alternating D-amino acids and L-amino acids and amino acid derivatives, such as aza-amino acids and azasulfuryl-amino acids. Optionally, the cyclic peptide mimetics may be conjugated to another agent via a linker to form cyclic peptide mimetic conjugates. The agent may be, for example, a chelating group to bind to a metal or an ion in a conjugate, which may be radioactive, which acts as an aid in diagnosis or treatment of an amyloidogenic disease. The agent may be also a thiol to bind a nanoparticle such as gold or iron nanoparticles acting as contrasting agents or as delivery vehicles.

According to an embodiment, the cyclic peptide mimetic has the structure c($X^1$-$X^2$-$X^3$-$X^4$-$X^5$-$X^6$) wherein: each of $X^1$, $X^2$, $X^3$, $X^4$, $X^5$, and $X^6$ is either an L-amino acid residue, a D-amino acid residue, or $X^7$; and wherein one of $X^1$, $X^2$, $X^3$, $X^4$, $X^5$, and $X^6$ is defined as $X^7$; and wherein the remaining $X^1$, $X^2$, $X^3$, $X^4$, $X^5$, and $X^6$ which are not defined as $X^7$ are amino acid residues in alternating L-configuration and D-configuration;

wherein $X^7$ is an aza-amino acid residue or azasulfuryl-amino acid residue having the structure:

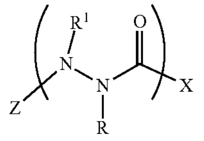

or

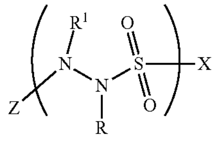

wherein the R group is the same R group as defined in naturally occurring and synthetic amino acids; $R^1$ is hydrogen, alkyl, aryl, heteroalkyl, heteroaryl, aryl alkyl or heteroaryl alkyl, or $R^1$ and R could together form a cyclic ring; Z is a carbonyl group of an adjacent amino acid residue; X is an amine group of an adjacent amino acid residue;

and wherein each of $X^1$, $X^2$, $X^3$, $X^4$, $X^5$, and $X^6$ is either unsubstituted or substituted by a conjugate moiety.

Additionally, described herein are methods for treatment and for diagnosis of amyloidogenic diseases comprising administering to a patient in need thereof a synthetic cyclic peptide mimetic or cyclic peptide mimetic conjugate as described.

The foregoing and other objects, features, and advantages will become more apparent from the following detailed description, which proceeds with reference to the accompanying figures.

The patent or application file contains at least one drawing executed in color. Copies of this patent or patent application publication with color drawing(s) will be provided by the Office upon request and payment of the necessary fee.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

I. Terms

Figures 1A, 1B, 1C, 1D:
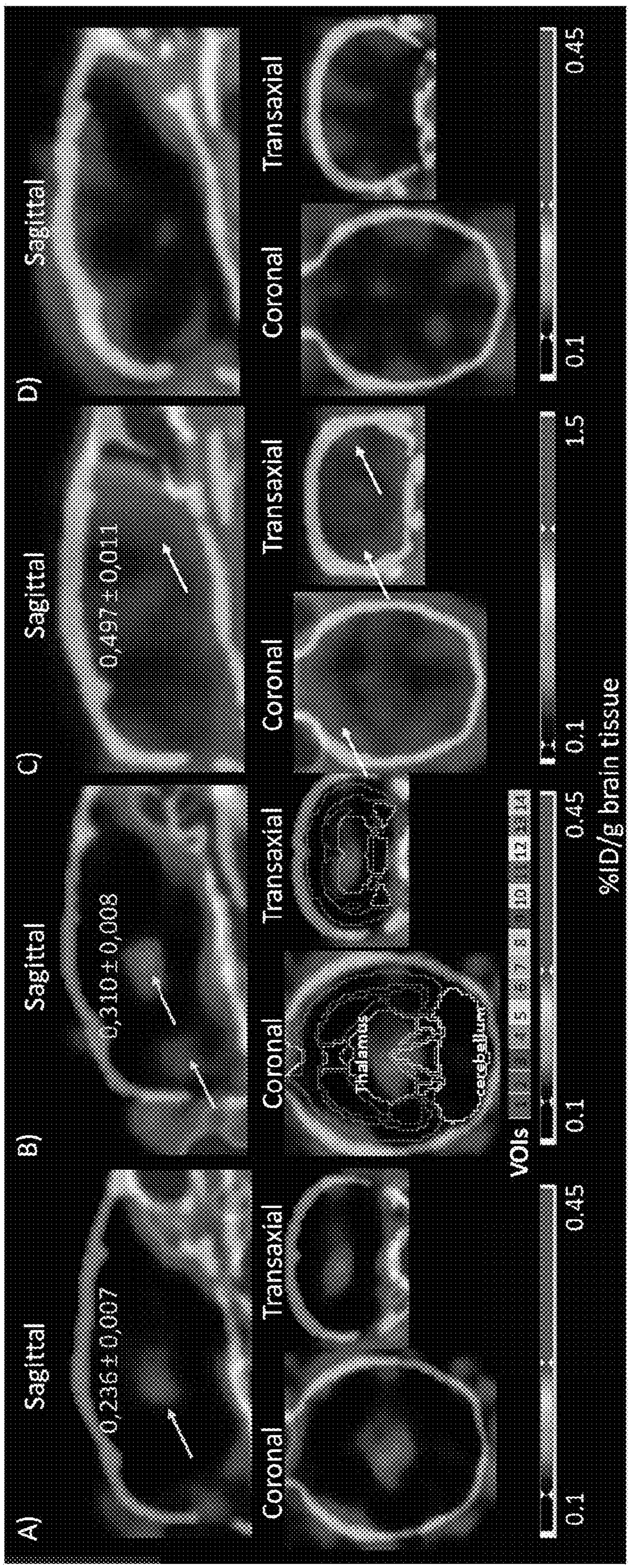
FIGS. 1A-1D show representative fused PET-CT images at 1-day post-injection of $^{64}$Cu-conjugate 43 formulated in sucrose/NaCl 0.9% (9% v/v) into (1A) 44 day- and (1B) 72 day-old female 5×FAD mouse monitoring progression of Aβ pathology; (1C) 40 min post-injection of $^{11}$C-PIB into 95-day-old 5×FAD mouse; (1D) 44-day-old WT female mouse at 1-day post-injection of $^{64}$Cu-conjugate 43. Green and blue represent highest and zero uptake. Yellow arrow points to Aβ species accumulation in thalamus. A different intensity scale was used for PET images with $^{11}$C-PIB. White arrows show accumulation of $^{11}$C-PIB in plaque at the cortex. In (1B), co-registration of experimental image data with brain mask to identify mouse atlas space was achieved to identify volumes of interest (VOI). 1. Striatum; 2. Cortex; 3. Hippocampus; 4. Thalamus; 5. Cerebellum; 6. Basal forebrain septum; 7. Hypothalamus; 8. Amygdala; 9. Brain stem; 10. Central gray; 11. Superior Collicili; 12. Olfactory bulb.

Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Amyloidogenic disease: a disease in which amyloid formation plays a role in its pathogenesis.

Aza-amino acid residue: An aza-amino acid residue is a derivative of an amino acid having the general structure:

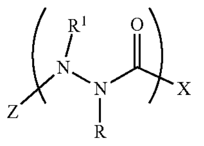

wherein the R group is the same R group as defined in naturally occurring and synthetic amino acids. Z is a carbonyl group of an adjacent amino acid residue. X is an amine group of an adjacent amino acid residue. $R^1$ is hydrogen, alkyl, aryl, heteroalkyl, heteroaryl, aryl alkyl and heteroaryl alkyl. Optionally, $R^1$ and R could together form a cyclic ring.

Azasulfuryl-amino acid residue: An azasulfuryl-amino acid is a derivative of an amino acid having the general structure:

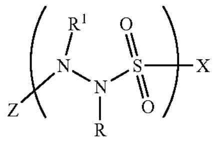

wherein the R group is the same R group as defined in naturally occurring and synthetic amino acids. Z is a carbonyl group of an adjacent amino acid residue. X is an amine group of an adjacent amino acid residue. $R^1$ is hydrogen, alkyl, aryl, heteroalkyl, heteroaryl, aryl alkyl and heteroaryl alkyl. Optionally, $R^1$ and R could together form a cyclic ring.

Chelating moiety: An agent capable of forming two or more coordinate bonds with a metal ion or a radioactive ion.

Conjugated moiety: A chelating moiety with a metal or radioactive metal, a fluorescent probe, a liposome, a nanoparticle, which can be covalently bond to a cyclic peptide mimetic through a corresponding amide group or other chemically stable bond such as lactone, ether, thioether, reduced amide, amine or disulfide bond.

Cyclic peptide: A polypeptide chain composed in a cyclic ring structure, which may be formed by linking one end of the peptide backbone or side chain to another end of the peptide backbone or side chain, using an amide bond or other chemically stable bond such as lactone, ether, thioether, reduced amide, amine or disulfide bond. Cyclic peptides may be composed of head-to-tail cyclization by amide bond formation between amine and carboxyl termini. Optionally, cyclic peptides comprise six amino acids and have six peptide bonds.

Cyclic peptide mimetic: A cyclic peptide comprising amino acids, which form a circular chain, and which comprises at least one amino acid derivative subunit, such as an azasulfuryl-amino acid residue or an aza-amino acid residue.

Hydrophobic amino acid: An amino acid possessing a nonpolar side chain. Hydrophobic amino acids include but are not limited to leucine (Leu), valine (Val), isoleucine (Ile), nor-leucine (Nle).

Metal or radioactive metal: A paramagnetic metal, a γ-emitting metal ion or a positron-emitting radionuclide, which may be complexed to the chelating moiety to be used for magnetic resonance imaging (MRI), single-photon emission computed tomography (SPECT), or positron emission tomography (PET) respectively.

Nanoparticle: A particle in the size range of 1 nanometer to 100 nanometers. Cyclic peptide mimetics may form conjugates comprising nanoparticles to be used for therapeutic uses or for imaging such as computerized tomography (CT) or MRI. Optionally, nanoparticles may be gold, magnetite or organic-based particles including liposomes, PGLA, serum-based particles and others. In the case of gold nanoparticles, the particles may be generated from reduction of gold salts with different reducing agents, such as citric acid, $NaBH_4$ or others. The surface of the nanoparticles may be coated with a polyethylene (PEG) molecule terminated with a carboxylic acid or an amine group, or another functional group which is covalently bond to a cyclic peptide mimetic through a corresponding amide group or other chemically stable bond such as lactone, ether, thioether, reduced amide, amine or disulfide bond.

Polar amino acid: An amino acid possessing a polar side chain in which a dipole moment exists because of differences in electronegativity between the bonded atoms. Polar amino acids include but are not limited to serine (Ser), threonine (Thr), cysteine (Cys) and aspartic acid (Asp).

Overview of Several Embodiments

Provided herein are some embodiments of the invention. U.S. Pat. No. 9,504,759, incorporated herein by reference, describes a cyclic D,L-α-peptide having six alternating amino acids in the D and L configuration having the structure: Cyclo-L-lysine-D-leucine-L-norleucine-D-tryptophan-L-histidine-D-serine. This compound is designated herein as compound 1.

Described herein are novel compounds having surprisingly increased amyloid beta binding activity. These novel compounds are cyclic peptide mimetics, preferably each composed of a total of 6 amino acids or amino acid derivatives, and each comprising an azasulfuryl-amino acid residue or an aza-amino acid residue. These novel compounds can be used as agents for treatment or diagnosis of amyloid diseases. Preferably, the amino acids are alternating D-amino acids and L-amino acids. Optionally, the amino acids or amino acid derivatives comprise at least one hydrophobic amino acid or amino acid derivative, and at least one polar amino acid or amino acid derivative. Optionally, three of the amino acids or amino acid derivatives in the cyclic peptide mimetic are hydrophobic amino acids or amino acid derivatives. Optionally, three of the amino acids or amino acid derivatives in the cyclic peptide mimetic are polar amino acids or amino acid derivatives.

Without being bound by theory, it is suggested that relative to parent amino amide, the semicarbazide or aminosulfamide residues (aza-amino amide or azasulfuryl-amino amide residues, respectively) have potential to increase Brønsted acid and Lewis base properties to improve intra- and intermolecular hydrogen bonding within peptide structures. It is suggested that aza- or azasulfuryl-derivatives of cyclic peptides described herein may increase intramolecular or intermolecular hydrogen bonding interactions, thereby destabilizing or stabilizing self-assembly of stacked rings to form tube-like structures, consequently increasing anti-amyloidogenic activity relative to “standard” cyclic peptides composed of only amino amide acid chains.

According to an embodiment, the cyclic peptide mimetics may further comprise a conjugate moiety bound to one of the amino acids or amino acid derivatives of the cyclic peptide mimetic, to form a peptide mimetic conjugate. The conjugate moiety may be bound through an amide, thiosulfide, ether, reduced amide, amine or thioether bond to one of the amino acid residues of the cyclic peptide mimetic, optionally, via an amine group of an R group of a lysine residue or carboxylate group of a R group of an aspartic acid or a glutamic acid residue.

The conjugate moiety may be a protein, a chelating moiety, an organic or inorganic nanoparticle, or a polymer. The polymer may be polyethylene glycol. The conjugate moiety may act as a therapeutic moiety, providing a biological activity on Aβ. Alternatively, the conjugate moiety may comprise a fluorescent probe or chelating moiety with a metal or radioactive metal, which can be detected using an imaging method.

Optionally, the chelating moiety is an agent is selected from the group consisting of: NOTA (2-[4,7-bis(carboxymethyl)-1,4,7-triazonan-1-yl]acetic acid) or its derivatives; DOTA (2-[4,7,10-tris(carboxymethyl)-1,4,7,10-tetrazacyclododec-1-yl]acetic acid) or its derivatives; methylhydroxamates derived from triaza- and tetraazamacrocycles ($NOTHA_2$ and $DOTHA_2$) or its derivatives; 1,4,7-triazacyclononane-1-glutaric acid-4,7-diacetic acid (NODAGA) or its derivatives; diethylenetriaminepentaacetate (DTPA) or it derivatives; 1,4,7,10-tetraazadodecane-1,4,7-triacetate (D03A) and its derivatives; 3,6,9,15-tetraazabicyclo[9.3.1]pentadeca-1 (1 5), 11,13-triene-3,6,9-triacetic acid) (PCTA) or its derivatives; 1,4,7,10-tetraazacyclotridecanetetraacetic acid (TRITA) and its derivatives; 1,4,8,11-tetraazacyclotetradecane-1,4,8,11-tetraacetic acid (TETA) and its derivatives; 1,4,7,10-tetraazadodecanetetramethylacetate (DOTMA) and its derivatives; 1,4,7,10-tetraazadodecane-1,4,7-trimethylacetate (D03MA) and its derivatives; N,N',N'',N'''-tetraphosphonatomethyl-1,4,7,10-tetraazacyclododecane (DOTP) and its derivatives; 1,4,7,10-tetraazacyclododecane-1,4,7,10-tetrakis(methylene methylphosphonic acid) (DOTMP) and its derivatives; 1,4,7,10-tetraazacyclododecane-1,4,7,10-tetrakis(methylene phenylphosphonic acid) (DOTPP) and its derivatives; or N,N'-ethylenedi-L-cysteine or its derivatives; and N1,N1'-(butane-1,4-diyl)bis(N4-hydroxy-N1-(3-(4-(hydroxy(methyl)amino)-4-oxobutanamido)propyl)-N4-methylsuccinamide) (4HSM) or its derivatives. Optionally, conjugates may be formed by conjugating a chelating agent with an amine group of a side chain of one of the amino acids.

According to an embodiment, the cyclic peptide mimetics may further be conjugated to a nanoparticle. The nanoparticle may be a gold nanoparticle, or other metal nanoparticle or an organic nanoparticle, such as a polymeric nanoparticle. For example, a cyclic peptide mimetic may be bound via an amide bond to a polyethylene glycol (PEG) molecule. The PEG molecule may form a surface coating of a nanoparticle such as a gold nanoparticle. Cyclic peptide mimetics may thereby be conjugated to nanoparticles, to be used as therapeutic or diagnostic agents. The nanoparticle may penetrate the blood-brain barrier and then be used as an imaging agent such as a contrast agent, for example in CT. The nano particle may have a size of below 100 nm, preferably between 20 and 50 nm.

According to an embodiment, the cyclic peptide mimetics may be conjugated to a liposome, and the liposome may comprise a contrast agent. The nanoparticle may also be formed from a protein such as albumin. Such microspheres are described in U.S. Pat. No. 9,504,759. The liposomes and the microspheres may have a size of below 100 nm, preferably between 20 and 50 nm According to an embodiment, a method of treatment is provided, comprising administering to a subject in need thereof, a cyclic peptide mimetic described herein, for the treatment of an amyloidogenic disease. Optionally, the disease is Alzheimer’s disease, Parkinson’s disease, or Huntington’s Disease. Optionally, the disease is a prion disease, systemic amyloidosis, cataract, or ALS.

According to an embodiment, the dose ranges between 1 mg to 1 g per dose. Doses may be administered daily, twice a week, three times a week, or once a week.

Optionally, the cyclic peptide mimetics may be administered through the oral, intravenous, intra peritoneal, intranasal, intraarterial, subcutaneous, intramuscular, intracranial, intraventricular, intraspinal, or intrathecal routes.

According to an embodiment, a method for imaging is provided, comprising administering to a subject in need thereof, a peptide mimetic conjugate in which the chelating agent is complexed to an atom such as a metal or a radioactive metal. The method may further comprise performing imaging on the subject. Optionally, the imaging may be PET; SPECT, or MRI. Optionally, the subject's brain and/or body undergoes imaging after administration of the peptide mimetic conjugate. Optionally, the peptide mimetic conjugate is complexed to a metal selected from the group consisting of: Copper-64, Copper-67, Gallium-67, Gallium-68, Antimony-117, Antimony-119, Scandium-43, Scandium-44, Scandium-47, Titanium-45, Indium-111, Samarium-153, Strontium-89, Yttrium-90, Lutetium-177, Bismuth-213, Gadolinium-153, and Actinium-225. Optionally, the subject is at risk of suffering from an amyloidogenic disease, optionally, Alzheimer's disease, Parkinson's disease, Huntington's Disease or systemic amyloidosis.

Copper-64 ($^{64}Cu$) is a suitable radionuclide for theranostic applications. $^{64}Cu$ ($\beta^+$, 0.65 MeV [17.8%] for PET imaging; $\beta^-$, 0.58 MeV [38.4%] along with Auger electrons [40%] for radiotherapy) has decay characteristics that allow its use for PET imaging and targeted radiotherapy. $^{64}Cu$ has a mean positron energy similar to that of $^{18}F$ and a half-life of 12.7 h, ideal for PET imaging and radiotherapy. $^{64}Cu$ emits a β particle with a short penetration range in tissue (2.5 mm) more suitable for relatively small masses. $^{64}Cu$ also emits a 6.84-keV Auger electron (40%) with a penetration range of about 5 μm, which may be highly toxic; most of this energy is delivered within a sphere of several nanometers around the decay site.

As mentioned above, R group is the same R group as defined in naturally occurring and synthetic amino acids.

R groups of representative amino acids are shown in table below with respect to exemplary naturally occurring and synthetic amino acids.

| Amino acid | R group of corresponding aza-amino acid residue or aza-sulfuryl aminio acid residue |
|---|---|
| Glycine | H |
| Alanine | $-CH_3$ |
| Aspartic acid | $-CH_2COOH$ |
| Glutamic acid | $-CH_2CH_2COOH$ |
| Phenylalanine | $-CH_2C_6H_5$ |
| Histidine | $-CH_2-C_3H_3N_2$ |
| Isoleucine | $-CH(CH_3)CH_2CH_3$ |
| Lysine | $-(CH_2)_4NH_2$ |
| Leucine | $-CH_2CH(CH_3)_2$ |
| Methionine | $-CH_2CH_2SCH_3$ |

-continued

| Amino acid | R group of corresponding aza-amino acid residue or aza-sulfuryl aminio acid residue |
|---|---|
| Asparagine | $-CH_2CONH_2$ |
| Proline | $-C_4H_8-$ |
| Glutamine | $-CH_2CH_2CONH_2$ |
| Arginine | $-(CH_2)_3NHC(=NH)NH_2$ |
| Valine | $-CH(CH_3)_2$ |
| Tyrosine | $-CH_2-C_6H_4OH$ |
| Norleucine | $-(CH_2)_3CH_3$ |
| Homoserine | $-CH_2CH_2OH$ |
| Triazole-3-alanine | $-CH_2-C_2H_2N_3$ |
| O-isopropyl-tyrosine | $-CH_2-C_6H_4OCH(CH_3)_2$ |
| Propargyl glycine | $-CH_2CCH$ |
| 4-fluoro phenylalanine | $-CH_2C_6H_4F$ |

Optionally, the cyclic peptide mimetics comprise at least one aza-amino acid residue or an azasulfuryl-amino acid residue comprising an R group selected from one of the R groups listed in the above table.

The following examples are provided to illustrate certain particular features and/or embodiments. These examples should not be construed to limit the disclosure to the particular features or embodiments described.

EXAMPLES

Example 1A: Cyclic Peptide Mimetics and their General Syntheses

Cyclic Peptide Mimetics described in Table 1 were prepared using the methods described herein. In Table 1, the following cyclic peptide mimetics were synthesized. Each peptide mimetic was given a code number. An asterisk next to the amino acid code indicates that it is an aza-amino acid residue. A caret next to the amino acid code indicates that it is an azasulfuryl-amino acid residue. Amino acid residues are indicated using their standard 3-letter code. For non-standard amino acids, the following codes are used: Nle is norleucine; Hse is homoserine, Tal is triazole-3-alanine, Itr is isotryptophan, IPrTyr is O-isopropyl-tyrosine, Pra is propargyl glycine, Nal is 1-naphthylalanine or 2-naphthylalanine, Orn is ornithine, and 4F-Phe is 4-fluoro phenylalanine. The amine group of amino acid/derivative in position 1 is linked via a peptide bond to the carbonyl group in position 6 to form a cyclic peptide mimetic.

TABLE 1

List of Cyclic Peptide Mimetics prepared.

| Code | Position 1 | Position 2 | Position 3 | Position 4 | Position 5 | Position 6 |
|---|---|---|---|---|---|---|
| 1 | D-Leu | L-Nle | D-Trp | L-His | D-Ser | Lys |
| 2 | D-Leu | L-Nle | D-Trp | L-His | D-Ser | Gly* |
| 3 | D-Leu | L-Nle | D-Trp | L-His | Gly* | L-Lys |
| 4 | D-Leu | L-Nle | D-Trp | Gly* | D-Ser | L-Lys |
| 5 | D-Leu | L-Nle | Gly* | L-His | D-Ser | L-Lys |
| 6 | D-Leu | Gly* | D-Trp | L-His | D-Ser | L-Lys |
| 7 | Gly* | L-Nle | D-Trp | L-His | D-Ser | L-Lys |
| 8 | D-Leu | L-Nle | D-Trp | L-His | D-Ser | Lys* |
| 9 | D-Leu | L-Nle | D-Trp | L-His | Hse* | L-Lys |
| 10 | D-Leu | L-Nle | D-Trp | L-His | IPrTyr* | L-Lys |
| 11 | D-Leu | L-Nle | D-Trp | D-His | IPrTyr* | L-Lys |
| 12 | D-Leu | L-Nle | D-Trp | Phe* | D-Ser | L-Lys |
| 13 | D-Leu | L-Nle | D-Trp | Tal* | D-Ser | L-Lys |
| 14 | D-Leu | L-Nle | D-Trp | Pra* | D-Ser | L-Lys |
| 15 | D-Leu | L-Nle | Itr* | L-His | D-Ser | L-Lys |
| 16 | D-Leu | Nle* | D-Trp | L-His | D-Ser | L-Lys |
| 17 | D-Leu | Phe* | D-Trp | L-His | D-Ser | L-Lys |

TABLE 1-continued

List of Cyclic Peptide Mimetics prepared.

| Code | Position 1 | Position 2 | Position 3 | Position 4 | Position 5 | Position 6 |
|---|---|---|---|---|---|---|
| 18 | Leu* | L-Nle | D-Trp | L-His | D-Ser | L-Lys |
| 19 | Phe* | L-Nle | D-Trp | L-His | D-Ser | L-Lys |
| 20 | 4F-Phe* | L-Nle | D-Trp | L-His | D-Ser | L-Lys |
| 55 | D-Leu | L-Nle | D-Trp | L-His | Gly^ | L-Lys |

Compounds 2-7 are cyclic peptide mimetics, which are modifications of compound 1 in that one amino acid residue was replaced with aza-Gly to form azacyclopeptides. Compounds 8, 9, 13, 15, 16 and 18, all are examples of cyclic peptides in which one of the amino acid residues of compound 1 was replaced by its corresponding aza-amino acid counterpart, with the exceptions of aza-homoserine (azaHse), aza-isotryptophan (azaltr) and aza-triazole-3-alanine (azaTal) which were used instead of the unstable aza-serine and aza-tryptophan residues, and the synthetically challenging of aza-histidine residue. Furthermore, compounds were prepared with aromatic ring side chain variations by the introduction of aza-Phe, aza-iPrTyr and aza-(4-fluoro)Phe residues relative to compound 1 to yield cyclic peptide mimetics 10-12, 17, 19 and 20. In addition, in compound 14, an aza-propargylglycine (azaPra) residue was introduced, as a potential handle for Copper-Catalyzed Azide Alkyne Cycloaddition (CuAAC) reactions for analog and conjugate synthesis. For example, CuAAC chemistry on the azaPra residue with different acetylenes may be used to make azaTal analogs bearing a substituent on one of the triazole ring nitrogen.

Figure 4A:
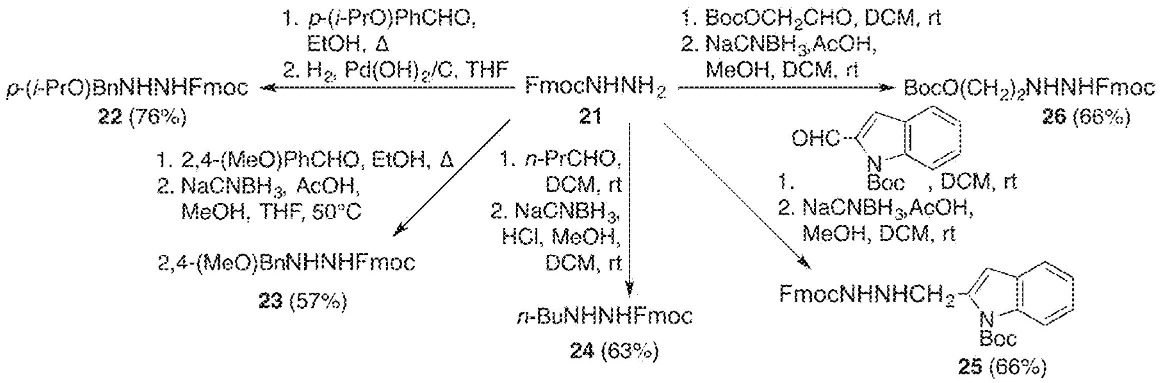
FIGS. 4A-4H depict schemes for synthesis of compounds and conjugates described herein.

For the introduction of aza-residues with side chains, N'-alkyl N-(Fmoc)hydrazines 27 and 33-36 (Schemes 2 and 3, FIGS. 4B, 4C) were synthesized from $FmocNHNH_2$ (21) using reductive amination conditions, and alkylation with propargylbromide. N'-Alkyl carbazates 22-26 were prepared by treating $FmocNHNH_2$ with the corresponding aldehyde and hydrogenation or hydride reduction of the imine intermediate in moderate to good yields (Scheme 1, FIG. 4A). The imine intermediates for carbazates 22-24 were prepared from commercially available aldehydes; for carbazates 25 and 26, the imines were respectively generated from N-Boc-indole-2-aldehyde and O-Boc-hydroxyacetaldehyde. For the synthesis of N-p-iso-propyloxybenzyl carbazate 22, the imine intermediate was reduced by hydrogenation (100 psi, $H_2$) using $Pd(OH)_2/C$ as a catalyst. For carbazates 23-26, imines were reduced using sodium cyanoborohydride in acidic reaction conditions.

Figure 4B:
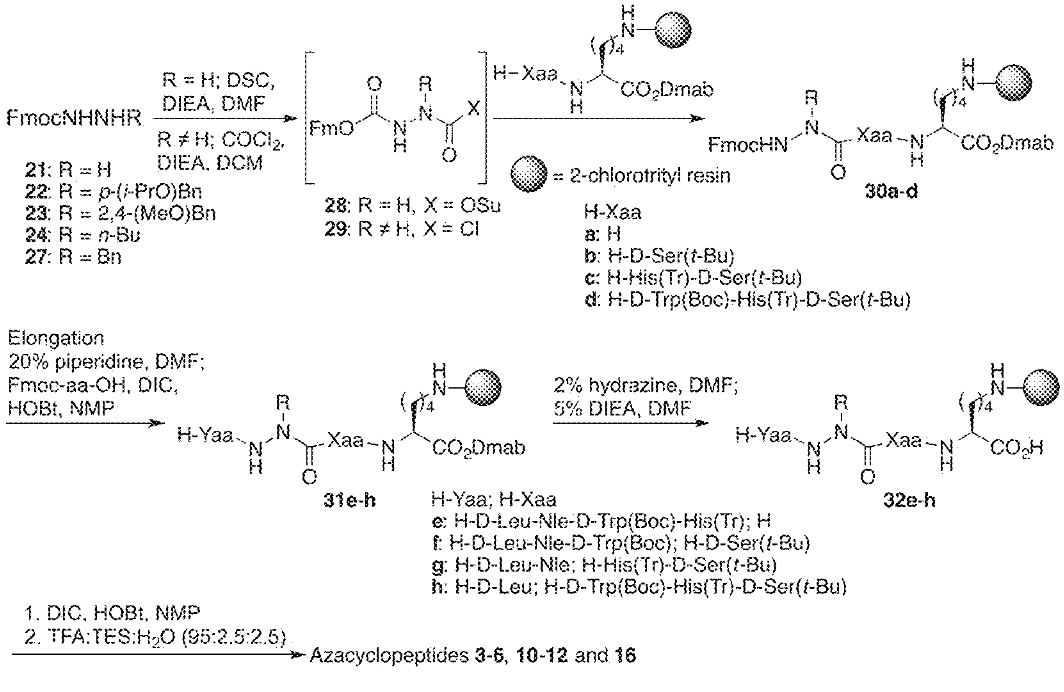
Figure 4C:
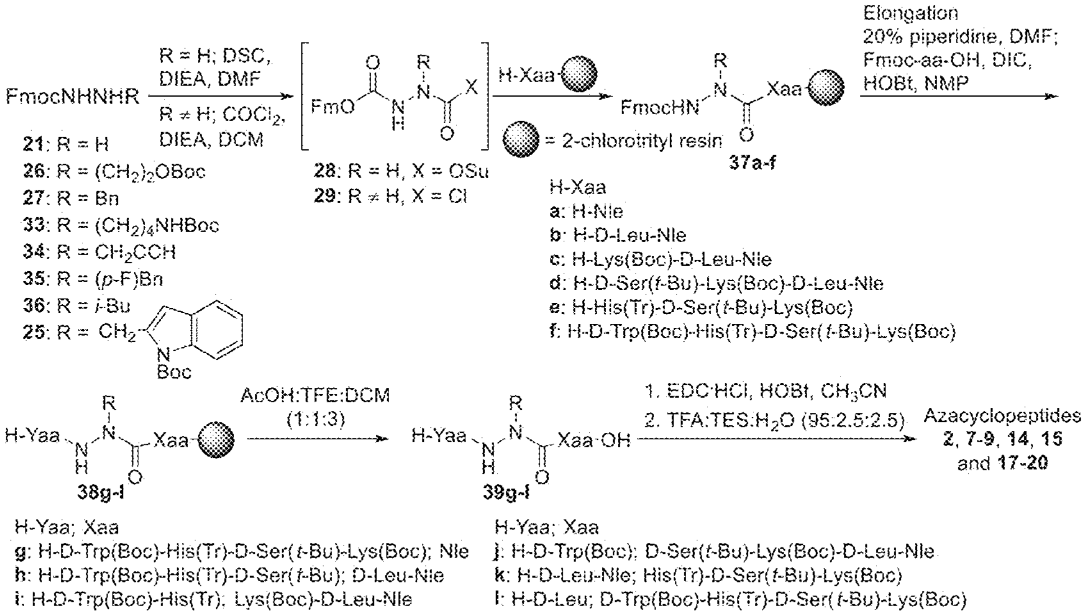

With $FmocNHNH_2$ (21) and N'-alkyl carbazates 22-27 and 33-36 in hand, azacyclopeptides were initially synthesized on acid labile 2-chlorotritylchloride resin by a route featuring aza-residue introduction, peptide elongation and head to tail cyclization on resin (Scheme 2, shown in FIG. 4B). Starting from Fmoc-Lys-ODmab resin, the sequence was prepared by elongation using standard solid-phase peptide synthesis methods. Aza-glycine residues were introduced into the sequence by activation of $FmocNHNH_2$ (21) with N,N'-disuccinimidyl carbonate (DSC) to provide activated carbazate 28, which was coupled to the peptide chain linked to the resin yielding azapeptide resins 30a-d (R═H). Employing DSC in the aza-glycine coupling protocol avoided intramolecular cyclization after activation of the aza-residue to form oxadiazolone, which has been observed using more reactive reagents such as carbonyldiimidazole (CDI) and phosgene. N'-Alkyl carbazates 22-24 and 27 were activated using phosgene in toluene to give their corresponding substituted aza-amino acid chlorides 29, which were coupled to peptide linked to resin to provide azapeptide resins 30a-d (R≠H).

After Fmoc group removal from 30a-d, amino acylation of the semicarbazide resin was achieved by treating the azaGly peptides (R═H) with N-(Fmoc)amino acid, DIC and HOBt in NMP; other azapeptides (R═H) were reacted with the symmetric amino acid anhydride that was generated in situ by treatment of the N-(Fmoc)amino acid with DIC. Elongation of the peptide sequence gave resin 31e-h, from which the Fmoc group was removed using 20% piperidine in DMF. During the synthesis of compound 3, after preparation of the azatripeptide Fmoc-His(Tr)-AzaGly-Lys-ODmab resin, attempts to remove the Fmoc group gave a product with a molecular ion corresponding to loss of HO-Dmab, likely due to an intramolecular attack by the α-nitrogen of the aza-glycine residue onto the Dmab-ester resulting in a hydantoin derivative. Related heterocycles have previously resulted from intramolecular cyclization of aza-glycine dipeptides in solution. Indirect evidence for such an intramolecular attack was provided by avoidance of loss of HO-Dmab upon protection of the α-nitrogen of the azaGly residue using 4-isopropoxybenzyl and 2,4-dimethoxybenzyl groups.

Subsequently, the Dmab group was removed by shaking the resin with 2% hydrazine in DMF, followed by treatment with 5% DIEA in DMF. Cyclization of azapeptide resins 32e-h was performed using DIC and HOBt in NMP. Resin cleavage, azapeptide precipitation and subsequent purification by reverse-phase HPLC provided the azacyclopeptide compounds 3-6, 10-12 and 16 (Table 1). In the synthesis of compound 3, the 2,4-dimethoxybenzyl group was removed during resin cleavage. The 4-isopropoxybenzyl group resisted acid solvolysis and two products having the same mass were isolated by HPLC. Diastereomer compounds 10 and 11 were likely formed due to epimerization during the coupling of the histidine residue onto the semicarbazide.

On-resin macrocyclization did not successfully provide the product on less nucleophilic semicarbazides at the 1-position (Leu*, compound 18). Moreover, the synthesis of azapeptides with aza-residues at the 6-position (Lys* compound 8) required an alternative anchoring strategy to the resin. A different synthetic route was developed consisting of azapeptide sequence elongation from the C-terminal carboxylate linked to 2-chlorotritylchloride resin, resin cleavage under mild conditions and cyclization in solution, before side chain removal (Scheme 3, FIG. 4C). Peptide sequences 37a-f were respectively prepared commencing from either Fmoc-Nle-OH (for 37a-d) or Fmoc-Lys(Boc)-OH (for 37e-f), which were added to 2-chlorotritylchloride resin using N,N'-diisopropylethylamine as a base in DCM. After acylation with activated carbazate 28 or aza-amino acid chlorides 29, the azapeptides were elongated using similar chemistry as described above. After Fmoc group removal, side chain protected linear sequences 38g-1 were cleaved from the resin using a cocktail of 1:1:3 AcOH:TFE:DCM. Macrocyclization was performed in solution on azapeptide 39g-1 using EDC·HCl and HOBt in acetonitrile under dilute reaction conditions to yield side chain protected azacyclopeptides. Macrocyclization in solution occurred typically with high conversion within a few hours to give cleaner product than cyclization on-resin, which necessitated repeated treatments and multiple days to effect completion. After removal of side chain protection with a 50% solution of TFA:TES:$H_2O$ (95:2.5:2.5) in DCM, azacyclopeptides 2, 7-9, 14, 15 and 17-20 were purified by reverse phase HPLC.

Yields, purity, retention time and mass spectrometric data are detailed below in Table 2. Retention times were determined by various methods. The method used is indicated in Table 2. Methods A-D and H on XTerra™ reverse-phase column (2.1 mm×50 mm, 3.5 μm, C18); Methods E-G on Atlantis reverse-phase column (3.9 mm×100 mm, 3.5 μm, C18). All the methods were run with a flow rate of 0.5 mL/min. Unless otherwise noted, method H was used for MeCN and method C was used for MeOH. Method A: 5-50% acetonitrile [0.1% formic acid (FA)] in water (0.1% FA) over 8 min followed by 50% acetonitrile (0.1% FA) in water (0.1% FA) over 1 min. Method B: 5-50% methanol [0.1% formic acid (FA)] in water (0.1% FA) over 8 min followed by 50% methanol (0.1% FA) in water (0.1% FA) over 1 min. Methods C and E: 10-90% methanol (0.1% FA) in water (0.1% FA) over 9 min followed by 90% methanol (0.1% FA) in water (0.1% FA) over 1 min. Method D: 30-95% methanol (0.1% FA) in water (0.1% FA) over 8 min followed by 95% methanol (0.1% FA) in water (0.1% FA) over 1 min. Method F: 20-90% acetonitrile (0.1% FA) in water (0.1% FA) over 9 min followed by 90% acetonitrile in water (0.1% FA) over 1 min. Methods G and H: 10-90% acetonitrile (0.1% FA) in water (0.1% FA) over 9 min followed by 90% acetonitrile in water (0.1% FA) over 1 min.

TABLE 2

Characterization of Compounds 2-20.

| Compound | Yield (%) | $RT^a$ (min) MeCN | $RT^a$ (min) MeOH | purity 214 nm | [M + $H^+$] and [M + $Na^+$] ions m/z (calcd) | m/z (obsd) |
|---|---|---|---|---|---|---|
| 2 | 15 | $7.19^A$ | 7.71 | >99 | 695.3624 | 695.3634 |
| 3 | 4 | $6.35^A$ | 6.57 | >99 | 736.4253 | 736.4263 |
| 4 | 2 | $7.26^A$ | $5.88^D$ | >95 | 686.3984 | 686.3995 |
| 5 | 4 | $4.38^F$ | $5.87^E$ | >99 | 637.3780 | 673.3782 |
| 6 | 4 | $3.83^A$ | $4.69^B$ | >99 | 710.3733 | 710.3740 |
| 7 | 6 | $4.88^A$ | $6.56^B$ | >99 | 710.3733 | 710.3747 |
| 8 | 9 | 4.21 | 6.22 | >99 | 766.4359 | 766.4371 |
| 9 | 10 | 4.50 | 6.77 | >99 | 780.4515 | 780.4522 |
| 10 | 1 | $7.17^A$ | 7.97 | >95 | 906.4961 | 906.4953 |
| 11 | 1 | $6.92^A$ | 7.68 | >95 | 884.5141 | 884.5171 |
| 12 | 3 | $6.17^A$ | $8.40^B$ | >91 | 776.4454 | 776.4468 |
| 13 | 8 | $7.26^G$ | $10.66^E$ | >99 | 767.4316 | 767.4324 |
| 14 | 10 | $5.12^A$ | $7.64^B$ | >99 | 724.4141 | 724.4157 |
| 15 | 7 | 4.61 | 6.74 | >99 | 766.4358 | 766.4372 |
| 16 | 1 | 5.74 | 6.22 | >99 | 766.4358 | 766.4359 |
| 17 | 6 | 4.36 | 6.28 | >99 | 800.4202 | 800.4219 |
| 18 | 8 | 5.38 | 5.38 | >99 | 766.4358 | 766.4368 |
| 19 | 10 | 5.87 | 8.91 | >99 | 822.4021 | 822.4035 |
| 20 | 13 | 4.53 | 6.56 | >99 | 818.4108 | 818.4126 |

Figure 4D:
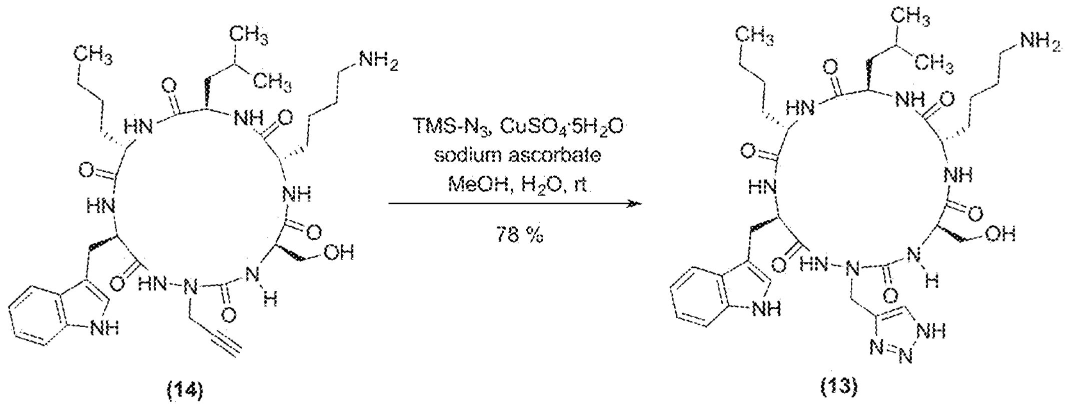

The utility of the alkyne of azaPra-cyclopeptide 14 was demonstrated by the synthesis of aza-triazole-3-alanine cyclopeptide compound 13 using CuAAC chemistry. Reaction of azaPra compound 14 with TMS-$N_3$ in the presence of $CuSO_4·5H_2O$ and sodium ascorbate in MeOH/water gave azacyclopeptide compound 13 in 78% yield after HPLC purification (Scheme 4, FIG. 4D). In principle, similar chemistry may be used to conjugate various azides onto the azaPra handle.

NOTA Conjugate Synthesis

Figure 4E:
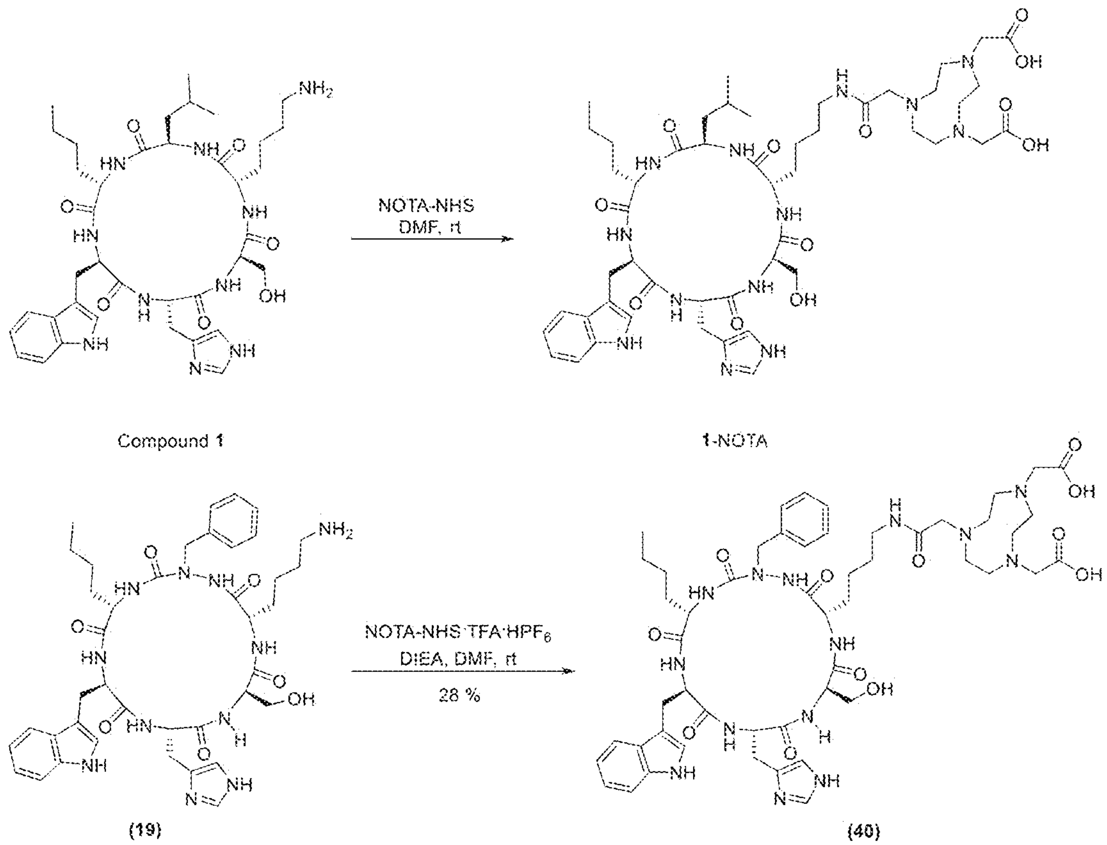

For the PET imaging studies to be addressed below, compound 1 and two azacyclopeptides, compounds 3 and 19 were coupled to NOTA through their lysine residues to obtain their corresponding NOTA conjugates, designated 1-NOTA, conjugate 43 and conjugate 40. 1-NOTA was obtained after HPLC purification of the reaction mixture from treatment of compound 1 in DMF with in-situ generated NOTA-NHS ester (Scheme 5, FIG. 4E). Conjugate 40 was obtained in 28% isolated yield after HPLC purification of the reaction mixture from treatment of compound 19 and DIEA in DMF with NOTA-NHS·TFA·$HPF_6$, which was obtained from commercial sources.

Figure 4F:
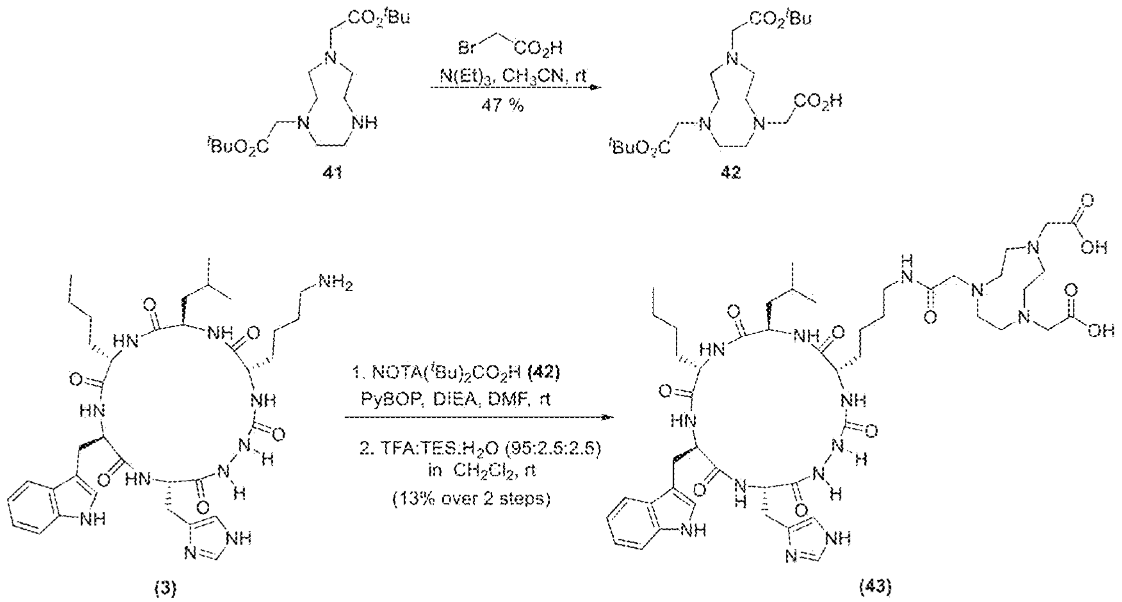

Alternatively, NOTA($^t$Bu)$_2$CO$_2$H (42) was prepared in 47% yield after HPLC purification from alkylation of triazacyclononane 41, using bromoacetic acid and triethylamine in acetonitrile (Scheme 6, FIG. 4F). Conjugate 43 was prepared in 13% isolated yield over two steps after HPLC purification from reacting the HCl salt of compound 3 with NOTA 42, PyBOP and DIEA in DMF, followed by tert-butyl ester solvolysis using a 50% solution of TFA:TES:$H_2O$ (95:2.5:2.5) in DCM.

Azasulfurylglycine Peptide Synthesis

Figure 4G:
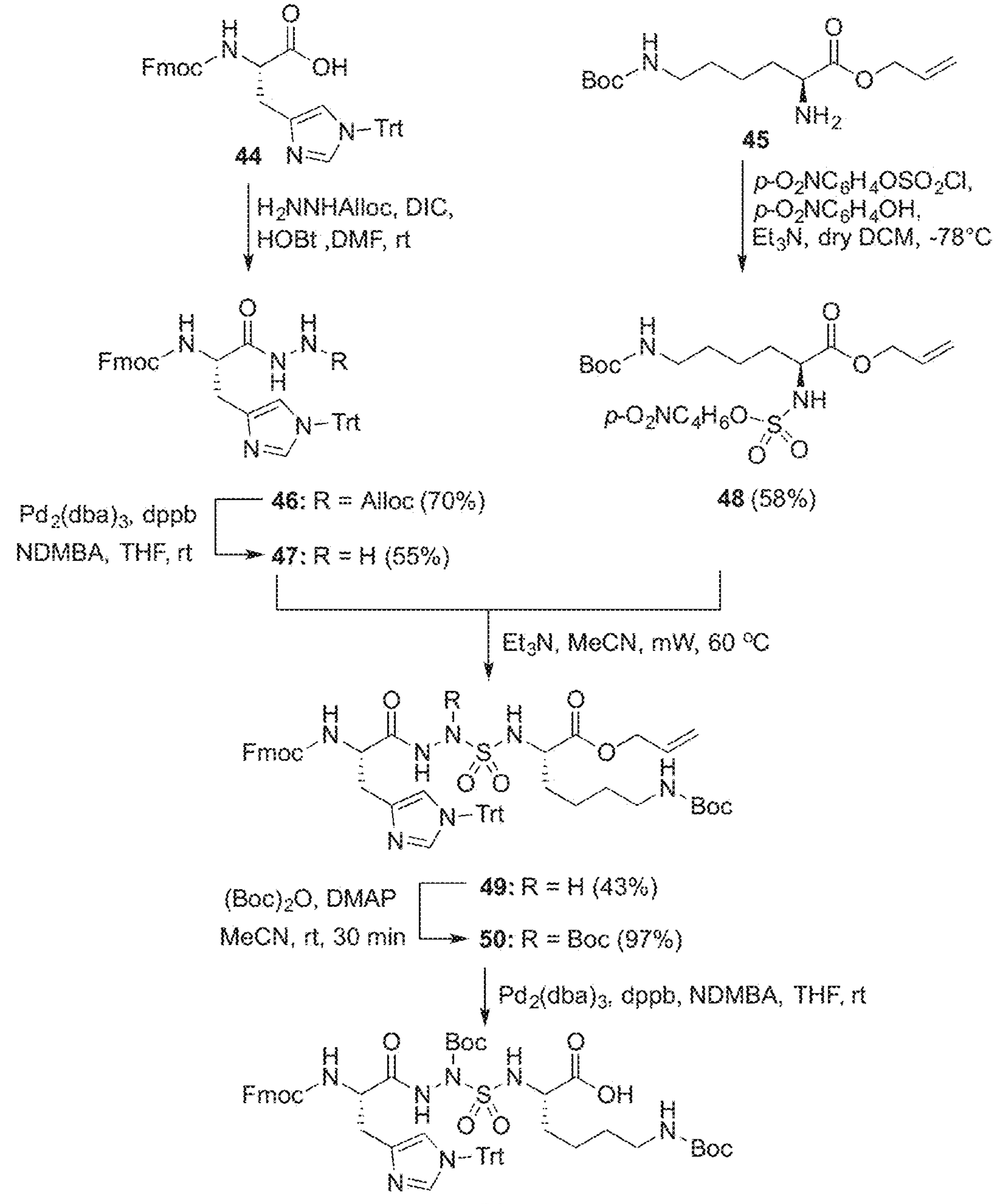
Figure 4H:
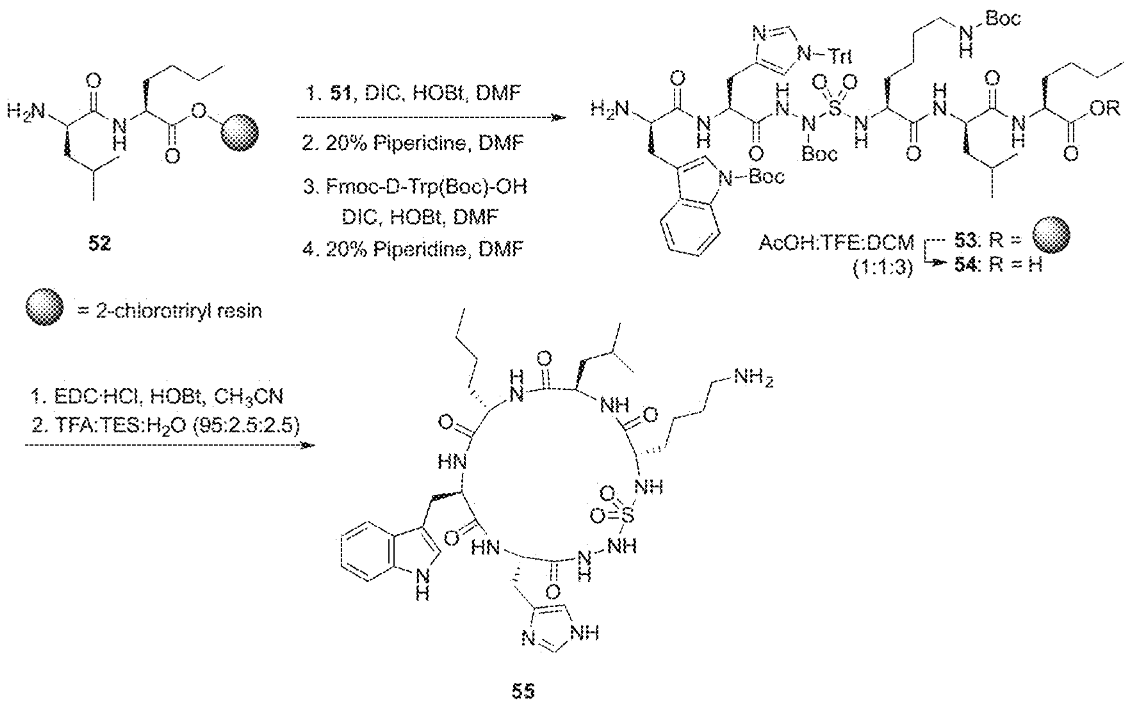

Considering the activity of compound 3, the corresponding azasulfurylglycine (AsG) analog compound 55 was targeted to enhance the Brønsted acidity and to add a second Lewis basic site on the amino amide surrogate (Schemes 7 and 8, FIGS. 4G and 4H). The synthesis of compound 55 was achieved by a route featuring preparation of protected azasulfuryl tripeptide building block 51.

First, Fmoc-His(Tr)-AsG-Lys(Boc)-OAllyl (49) was assembled by coupling $N^\alpha$-Fmoc-$N^\tau$-trityl-L-histidine hydrazide (47) and p-nitrophenylsulfamidate allyl ester 48. Hydrazide 47 was obtained from acylation of allyl carbazate with $N^\alpha$-Fmoc-$N^\tau$-trityl-L-histidine 44 and Alloc group removal was performed using tris(dibenzylideneacetone) dipalladium(0) [$Pd_2(dba)_3$], 1,4-bis(diphenylphosphino)butane (dppb) and N,N'-dimethylbarbituric acid (NDMBA) in THF (Scheme 7, FIG. 4G). The reaction of sulfamidate 48 with hydrazide 47 was performed under microwave irradiation in the presence of triethylamine in acetonitrile. Subsequently, azasulfuryl tripeptide 51 was prepared by protection of the sulfamide nitrogen with a Boc group and allyl ester removal using palladium catalysis as described above. Azasulfuryl tripeptide 51 was coupled to H-D-Leu-Nle-2-chlorotritylchloride resin 52 using DIC and HOBt in DMF, elongated and cleaved from the resin to afford linear peptide 54, which was cyclized, deprotected and purified as described for azacyclopeptides 2, 7-9, 14, 15 and 17-20 above to provide compound 55, as in Scheme 8, FIG. 4H.

Example 1B: Synthesis of Compounds of Table 1

General Procedure for Amino Acid Couplings and Fmoc Deprotection. Peptide synthesis was performed under standard conditions in an automated shaker using 2-chlorotrityl chloride resin. Couplings of amino acids (3 equiv.) were performed using DIC (3 equiv.) and HOBT (3 equiv.) in DMF or NMP. Fmoc group removal was performed by treating the resin with 20% piperidine in DMF for a period of 20 min (2×). Resin was washed after each coupling and deprotection step sequentially using DMF (3×), MeOH (3×), and DCM (3×).

General Procedure for Side Chain Deprotection and Azapeptide Cleavage. Azapeptide resin was treated with a freshly made solution of TFA/$H_2O$/TES (95:2.5:2.5, v/v/v, 20 mL/g of azapeptide resin) for 2 h at room temperature. The resin was filtered and washed with neat TFA. The filtrate and washings were concentrated to a volume of about 1 mL and treated with $Et_2O$. The precipitate was filtered, washed with $Et_2O$, dissolved in an acetonitrile/$H_2O$ (1:1, v/v) solution, and freeze-dried to a light foam or powder.

Compound 6

Fmoc-D-Trp(Boc)-His(Tr)-D-Ser(1-Bu)-Lys(2-chlorotrityl resin)-ODmab was synthesized starting from Fmoc-Lys (2-chlorotrityl resin)-ODmab (0.32 mmol) by sequential Fmoc group deprotections with 20% piperidine in DMF, and couplings using Fmoc-D-Ser($O^tBu$)-OH, Fmoc-His(Trt)-OH and Fmoc-D-Trp(Boc)-OH with DIC (3 eq.) and HOBt (3 eq.) in NMP according to the general protocol. The resin aliquot was cleaved as described above using TFA/TES/$H_2O$ (95:2.5:2.5) and analyzed by UV-HPLC which indicated Fmoc-D-Trp-His-D-Ser-Lys-ODmab was of approximately 70% purity: RT 9.00 min on a Sunfire column using a gradient of 5-50% MeCN (0.1% FA) in water (0.1% FA) over 14 min. After removal of the Fmoc group, the peptide was treated with active carbazate 28 as described below.

A solution of DSC (3 eq., 246 mg. 0.96 mmol) in dry DMF (4 mL) was treated dropwise with a solution of N-(Fmoc)hydrazine (21, 3 eq., 248 mg, 0.96 mmol) in dry DMF (5 mL) over 10-15 min at 0° C. under inert atmosphere. The reaction mixture was stirred at room temperature for 1 h and transferred to a syringe tube equipped with a Teflon™ filter, stopper and stopcock containing H-D-Trp (Boc)-His(Tr)-D-Ser(1-Bu)-Lys(2-chlorotrityl resin)-ODmab (1 eq., 600 mg, 0.32 mmol) in DMF (4 mL). The resin mixture was then treated with DIEA (6 eq., 0.33 mL, 1.92 mmol), shaken on an automated shaker for 14-16 h, and filtered. After filtration, the resin was washed sequentially with DMF (3×), MeOH (3×) and DCM (3×), and dried under vacuum, to afford aza-glycine resin 30d (R═H). Cleavage and analysis of an aliquot of resin 30d (R═H) by HPLC indicated the absence of the starting material and Fmoc-azaGly-D-Trp-His-D-Ser-Lys-ODmab of 50% purity at RT 8.9 min on a Sunfire column with a gradient of 5-50% MeCN (0.1% FA) in water (0.1% FA) over 14 min.

After removal of the Fmoc group from azapeptide 30d (R═H), peptide coupling was continued with Fmoc D-Leu-OH using DIC (3 eq.) and HOBt (3 eq.) in NMP to provide Fmoc-D-Leu-azaGly-D-Trp(Boc)-His(Tr)-D-Ser(1-Bu)-Lys (2-chlorotrityl resin)-ODmab, from which an aliquot was cleaved and analyzed by HPLC, which indicated formation of Fmoc-D-Leu-azaGly-D-Trp-His-D-Ser-Lys-ODmab at RT 9.3 min on a Sunfire column with a gradient of 5-50% MeCN (0.1% FA) in water (0.1% FA) over 14 min.

After the Fmoc group removal, the Dmab group was removed from resin 31h (R═H) using 2% hydrazine in DMF (3×15 min), followed by 5% DIEA in DMF (3×15 min). Resin 32h (R═H) was washed sequentially with DMF (3×), MeOH (3×) and DCM (3×), and dried: ES-MS analysis of a cleaved resin aliquot presented m/z=728.47. The head to tail cyclization of the linear peptide on resin 32h (R═H, 1 eq., ~550 mg. 0.32 mmol) was performed by two consecutive treatments with DIC (3 eq.) and HOBt (3 eq.) in NMP for 16 h. The resin was washed, dried, and treated with 10 mL of a freshly made solution of TFA/TES/$H_2O$ (95:2.5:2.5) for 2 h. The resin was filtered and washed with TFA (10 mL). The filtrate and washes were combined and concentrated to a residue, that was triturated with diethyl ether to give a light-yellow solid, which was purified by reverse phase HPLC on a Gemini® C18 column (Phenomenex® Inc., pore size 110 Å, particle size: 5 μm, 250×21.2 mm) using a binary solvent system consisting of a gradient of 10%-60% MeCN (0.1% FA) in water (0.1% FA), with a flow rate of 10 mL/min, and UV detection at 214 nm. The desired fractions were combined and freeze-dried to give 9.2 mg (4% yield) of compound 6 as white fluffy solid: analytical RP-HPLC on an XTerra™ column 3.5 μm (2.1×50 mm), >99% purity at RT=3.83 min using a gradient of 5-50% MeCN (0.1% FA) in water (0.1% FA) over 8 min; 99.6% purity at RT=4.69 min with a gradient of 5-50% MeOH (0.1% FA) in water (0.1% FA) over 8 min; HRMS m/z calcd. For $C_{33}H_{48}N_{11}O_7$ $[M+H]^+$ 710.3733, found 710.3740.

Compound 4

Aza-glycine containing compound 4 was synthesized using the same procedure as that described for the synthesis of compound 6 using H-D-Ser(t-Bu)-Lys(2-chlorotrityl resin)-ODmab, which was prepared from Fmoc-Lys(2-chlorotrityl resin)-ODmab (0.32 mmol). The crude product was purified by reverse phase HPLC on a Gemini® C18 column (Phenomenex® Inc., pore size 110 Å, particle size: 5 μm, 250×21.2 mm) using a binary solvent system consisting of a gradient of 10% to 60% MeCN (0.1% FA) in water (0.1% FA), with a flow rate of 10 mL/min and UV detection at 214 nm. The desired fractions were combined and freeze-dried to give 3.3 mg (1.5% yield) of Compound 4 as white fluffy solid: analytical RP-HPLC on an XTerra™ column 3.5 μm (2.1×50 mm), >95% purity at RT=7.26 min using a gradient of 5-50% MeCN (0.1% FA) in water (0.1% FA) over 8 min; >97% purity at RT=5.88 min with a gradient of 30-95% MeOH (0.1% FA) in water (0.1% FA) over 8 min; HRMS m/z calcd. For $C_{33}H_{52}N_9O_7$ $[M+H]^+$ 686.3984, found 686.3995.

Compound 5

Aza-glycine containing compound 5 was synthesized using the same procedure as that described for the synthesis of [azaGly[5]]-CP-2 (6) using H-His(Tr)-D-Ser(t-Bu)-Lys(2-chlorotrityl resin)-ODmab, which was prepared from Fmoc-Lys(2-chlorotrityl resin)-ODmab (0.30 mmol). The crude product was purified by reverse phase HPLC on a Gemini® C18 column (Phenomenex® Inc., pore size 110 Å, particle size: 5 μm, 250×21.2 mm) using a binary solvent system consisting of a gradient of 10-60% MeCN (0.1% FA) in water (0.1% FA) with a flow rate of 6 mL/min and UV detection at 214 nm. The desired fractions were combined and freeze-dried to give 8.1 mg (4% yield) of compound 5 as white fluffy solid: analytical RP-HPLC on an Atlantis column 3.5 μm (3.9×100 mm), >99% purity at RT=4.38 min using a gradient of 20-90% MeCN (0.1% FA) in water (0.1% FA) over 8 min; 100% purity at RT=5.87 min using a gradient of 10-90% MeOH (0.1% FA) in water (0.1% FA) over 8 min; HRMS m/z calcd. For $C_{28}H_{49}N_{10}O_7$ $[M+H]^+$ 637.378, found 637.3782.

Compound 3

A solution of N-fluorenylmethyl-N'-(2,4-dimethoxybenzyl) carbazate (23, 3 eq., 364 mg, 0.90 mmol) in dry DCM (10 mL) under inert atmosphere at 0° C. was treated dropwise with a solution of phosgene in toluene (20% w/v, 6 eq., 0.83 mL, 1.8 mmol), and stirred for 15-30 min, when complete consumption of the starting carbazate was observe by TLC and the reaction mixture was concentrated under reduced pressure. The residue containing aza-amino acid chloride 29 was dissolved in dry DCM (10 mL), treated with DIEA (12 eq., 0.63 mL, 3.6 mmol), and transferred to a syringe tube equipped with a Teflon™ filter, stopper and stopcock containing H-Lys(2-chlorotrityl resin)-ODmab (1 eq., 0.3 mmol) swollen in DCM (5 mL). The swollen resin mixture was shaken on an automated shaker for 12 h, filtered, washed, and dried to provide resin 30a (R=Dmb), which was confirmed by ES-MS analysis (Fmoc-azaGly-Lys-ODmab: m/z=738) of an aliquot of resin cleaved and examined by UV-HPLC, which showed the absence of starting material and a prominent peak at RT 9.307 min on a Sunfire column with a gradient of 5-50% MeCN (0.1% FA) in water (0.1% FA) over 14 min. Aza-(2,4-dimethoxy) phenylalanine resin 30a.

After removal of the Fmoc group, peptide coupling was continued using DIC (3 eq.) and HOBt (3 eq.) in NMP. After removal of last Fmoc group, the Dmab group was removed from resin using 2% hydrazine in DMF (3×15 min), followed by 5% DIEA in DMF (3×15 min). Resin was washed sequentially with DMF (3×), MeOH (3×) and DCM (3×), and dried. The head to tail cyclization of the linear peptide on resin was performed by two consecutive treatments with DIC (3 eq.) and HOBt (3 eq.) in NMP for 16 h. The resin was washed, dried, and treated with 10 mL of a freshly made solution of TFA/TES/$H_2O$ (95:2.5:2.5) for 2 h. The resin was filtered and washed with TFA (10 mL). The filtrate and washes were combined and concentrated to a residue.

Purification was performed on reverse phase HPLC on a Gemini® C18 column (Phenomenex® Inc., pore size: 110 Å, particle size: 5 μm, 250×21.2 mm) using a binary solvent system consisting of a gradient of 10-60% MeCN (0.1% FA) in water (0.1% FA) with a flow rate of 10 mL/min and UV detection at 214 nm. The desired fractions were combined and freeze-dried to give 9.0 mg (4% yield) of compound 3 as white fluffy solid: analytical RP-HPLC on XTerra™ column 3.5 μm (2.1×50 mm), >99% purity at RT=6.35 min using a gradient of 5-50% MeCN (0.1% FA) in water (0.1% FA) over 8 min; >99% purity at RT=6.57 min using a gradient of 10-90% MeOH (0.1% FA) in water (0.1% FA) over 9 min; HRMS m/z calcd. For $C_{36}H_{54}N_{11}O_6$ $[M+H]^+$ 736.4253, found 736.4263.

Compounds 10 and 11

Aza-O-iso-propyl-tyrosine compounds 10 and 11 were synthesized using the same procedure as that described for the synthesis of compound 3 using H-Lys(2-chlorotrityl resin)-ODmab, which was prepared from Fmoc-Lys(2-chlorotrityl resin)-ODmab (0.28 mmol). Purification was performed on reverse phase HPLC on a Gemini® C18 column (Phenomenex® Inc., pore size: 110 Å, particle size: 5 μm, 250×21.2 mm) using a binary solvent system consisting of a gradient of 10-60% MeCN (0.1% FA) in water (0.1% FA) with a flow rate of 10 mL/min and UV detection at 214 nm. Two different peaks were collected with same mass (m/z=884), both separately lyophilized to give 1.3 mg (0.6% yield) of compound 11 as white fluffy solid: analytical RP-HPLC on XTerra™ column 3.5 μm (2.1×50 mm), >95% purity at RT=6.92 min using a gradient of 5-50% MeCN (0.1% FA) in water (0.1% FA) over 8 min; >99% purity at RT=7.69 min using a gradient of 10-90% MeOH (0.1% FA) in water (0.1% FA) over 9 min; HRMS m/z calcd. For $C_{46}H_{66}N_{11}O_7$ $[M+H]^+$ 884.5141, found 884.5171 and 1.5 mg (0.7% yield) of Compound 10 as white fluffy solid: analytical RP-HPLC on XTerra™ column 3.5 μm (2.1×50 mm), >95% purity at RT=7.17 min using a gradient of 5-50% MeCN (0.1% FA) in water (0.1% FA) over 8 min; >99% purity at RT=7.97 min using a gradient of 10-90% MeOH (0.1% FA) in water (0.1% FA) over 9 min; HRMS m/z calcd. For $C_{46}H_{65}N_{11}O_7Na$ $[M+H]^+$ 906.4961, found 906.4953. The D- and L-His isomers were assigned arbitrarily to 10 and 11 having the shortest and longest retention times.

Compound 12

Aza-phenylalanine compound 12 was synthesized using the same procedure as that described for the synthesis of compound 3 using H-D-Ser(t-Bu)-Lys(2-chlorotrityl resin)-ODmab, which was prepared from Fmoc-Lys(2-chlorotrityl resin)-ODmab (0.055 mmol). The crude product was purified by reverse phase HPLC on a Gemini® C18 column (Phenomenex® Inc., pore size 110 Å, particle size: 5 μm, 250×21.2 mm) using a binary solvent system consisting of a gradient of 5-60% MeOH (0.1% FA) in water (0.1% FA) with a/flow rate of 6 mL/min and UV detection at 214 nm. The desired fractions were combined and freeze-dried to give 1.28 mg (3% yield) of compound 12 as white fluffy solid: analytical RP-HPLC on a XTerra™ column 3.5 μm (3.9×100 mm), 100% purity at RT=6.17 min using a gradient of 5-50% MeCN (0.1% FA) in water (0.1% FA) over 9 min; >91% purity at RT=8.40 min using a gradient of 5-50% MeOH (0.1% FA) in water (0.1% FA) over 14 min; HRMS m/z calcd. For $C_{40}H_{58}N_9O_7$ $[M+H]^+$ 776.4454, found 776.4468.

Compound 16

Aza-norleucine peptide 16 was synthesized using the same procedure as that described for the synthesis of compound 3 using H-D-Trp(Boc)-His(Tr)-D-Ser(t-Bu)-Lys(2-chlorotrityl resin)-ODmab, which was prepared from Fmoc-Lys(2-chlorotrityl resin)-ODmab (0.296 mmol). The crude product was purified by reverse phase HPLC on a Gemini® C18 column (Phenomenex® Inc., pore size 110 Å, particle size: 5 μm, 250×21.2 mm) using a binary solvent system consisting of a gradient of 10-60% MeCN (0.1% FA) in water (0.1% FA) with a flow rate of 6 mL/min and UV detection at 214 nm. The desired fractions were combined and freeze-dried to give 3.0 mg (1% yield) of compound 16 as white fluffy solid: analytical RP-HPLC on an XTerra™ column 3.5 μm (2.1×50 mm), >99% purity at RT=5.74 min using a gradient of 10-90% MeCN (0.1% FA) in water (0.1% FA) over 9 min; >99% purity at RT=6.22 min using a gradient of 10-90% MeOH (0.1% FA) in water (0.1% FA) over 9 min; HRMS m/z calcd. For $C_{37}H_{56}N_{11}O_7$ $[M+H]^+$ 766.4358, found 766.4359.

Compound 7

A solution of Fmoc-Nle-OH (1 eq., 1 g, 2.83 mmol) and DIEA (3 eq., 1.5 mL, 8.49 mmol) in DCM (20 mL) was added to 2-chlorotrityl chloride polystyrene resin (2.86 g, 0.79 mmol/g), and the mixture was agitated for 16 h. The Fmoc-Nle resin was filtered, washed, and dried. After removal of the Fmoc group, H-Nle-O-2-chlorotrityl resin (0.30 mmol) was treated with active carbazate 28 [prepared as described above from N-(Fmoc)hydrazine (21, 3 eq., 229 mg, 0.90 mmol), DSC (3 eq., 231 mg, 0.90 mmol) and DIEA (6 eq., 0.32 mL, 1.8 mmol) in dry DMF (10 mL)] and agitated for 16 h, when ES-MS analysis of a cleaved resin aliquot indicated formation of Fmoc-aza-Gly-Nle-OH (m/z 412) and a significant peak by UV-HPLC at RT 10.042 min on a Sunfire column with a gradient of 5-50% MeCN (0.1% FA) in water (0.1% FA) over 14 min. After Fmoc group removal, azaGly resin 37a (R═H) was elongated respectively with Fmoc-Lys(Boc)-OH, Fmoc-D-Ser(1-Bu)-OH, Fmoc-His(Trt)-OH and Fmoc-D-Trp(Boc)-OH using DIC (3 eq.) and HOBt (3 eq.) in NMP. Analysis of a cleaved resin aliquot by UV-HPLC and ES-MS indicated formation of Fmoc-D-Trp-His-D-Ser-Lys-aza-Gly-Nle-OH: m/z=950.53, purity ~85%, RT=7.6 min on a XTerra™ column 3.5 μm (2.1×50 mm) using a gradient of 5-50% MeCN (0.1% FA) in water (0.1% FA) over 8 min. After Fmoc group removal, resin 38g (R═H), was treated with a mixture of AcOH/TFE/DCM (1:1:3, 10 mL) for 30 min (2×). Filtration and washing of the resin, followed by evaporation of the filtrate and washings gave 350 mg of a residue containing azapeptide 39g (R═H). The residue was dissolved in MeCN (200 mL), treated with EDC·HCl (173 mg, 0.90 mmol, 3 eq.) and HOBt (122 mg, 0.90 mmol, 3 eq.), stirred at room temperature overnight and concentrated to a residue, analysis of which by ES-MS indicated cyclization (m/z=710.60). The residue was dissolved in DCM (10 mL), treated with 10 mL of a solution of TFA/TES/$H_2O$ (95:2.5:2.5) for 4 h, and concentrated to a residue that was triturated with diethyl ether to provide a light-yellow solid, which was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA) with a flow rate of 6 mL/min and UV detection at 214 nm. The desired fractions were combined and freeze-dried to provide 13 mg (6% yield) of compound 7 as white fluffy solid: by analytical RP-HPLC on XTerra™ column 3.5 μm (2.1×50 mm), >99% purity at RT=4.88 min using a gradient of 5-50% MeCN (0.1% FA) in water (0.1% FA) over 8 min; >99% purity at RT=6.56 min using a gradient of 5-50% MeOH (0.1% FA) in water (0.1% FA) over 8 min; HRMS m/z calcd. for $C_{33}H_{48}N_{11}O_7$ $[M+H]^+$ 710.3733, found 710.3747.

Compound 2

Aza-glycine compound 2 was synthesized using the same procedure as that described for the synthesis of compound 7 using H-D-Leu-Nle-O-2-chlorotrityl resin, which was prepared from H-Nle-O-2-chlorotrityl resin (0.57 mmol). The crude product was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA) with a flow rate of 10 mL/min and UV detection at 214 nm. The desired fractions were combined and freeze-dried to provide 60 mg (15% yield) of compound 2 as white fluffy solid: analytical RP-HPLC on XTerra™ column 3.5 μm (2.1×50 mm), >99% purity at RT=7.19 min using a gradient of 5-50% MeCN (0.1% FA) in water (0.1% FA) over 8 min; >99% purity at RT=7.71 min using a gradient of 10-90% MeOH (0.1% FA) in water (0.1% FA) over 8 min; HRMS m/z calcd. for $C_{33}H_{47}N_{10}O_7$ $[M+H]^+$ 695.3624, found 695.3634.

Compound 18

A solution of N-fluorenylmethyl-N'-(isobutyl) carbazate (36, 3 eq., 265 mg, 0.85 mmol) in dry DCM (10 mL) under inert atmosphere at 0° C. was treated dropwise with a solution of phosgene in toluene (20% w/v, 6 eq., 0.85 mL, 1.7 mmol), and stirred for 15-30 min, when complete consumption of the starting carbazate was observe by TLC and the reaction mixture was concentrated under reduced pressure. The residue containing the aza-amino acid chloride 29 was dissolved in dry DCM (10 mL), treated with DIEA (12 eq., 0.59 mL, 3.42 mmol), and transferred to a syringe tube equipped with a Teflon™ filter, stopper and stopcock containing H-Nle-O-2-chlorotrityl resin (0.285 mmol) swollen in DCM (5 mL). The swollen resin mixture was shaken on an automated shaker for 12 h, filtered, washed, and dried to provide resin 37a (R═i-Bu), which was confirmed on an aliquot of cleaved resin, which by LC-MS analysis (Fmoc-aza-Leu-Nle-OH: m/z=468.2) exhibited an absence of the starting material peak and a prominent peak at RT 11.16 min on an Agilent Poroshell reverse-phase column (4.6 mm×50 mm, 2.7 μm, C18) with a gradient of 10-90% MeCN (0.1% FA) in water (0.1% FA) over 14 min. Fmoc-aza-Leu-Nle-O-2-chlorotrityl resin 37a (R═i-Bu) was elongated, cyclized, and cleaved. Mild cleavage was performed in AcOH: TFE:DCM (1:1:3), followed by evaporation of volatiles and cyclization in solution (EDC/HOBT in CH3CN). Purification was performed using reverse phase HPLC on a Gemini® C18 column (Phenomenex® Inc., pore size: 110 Å, particle size 5 μm, 250×21.2 mm) using a binary solvent system consisting of a gradient of 10-60% MeCN (0.1% FA) in water (0.1% FA) with a flow rate of 10 mL/min and UV detection at 214 nm. The desired fractions were combined and freeze-dried to give 18.0 mg (8% yield) of compound 18 as white fluffy solid: analytical RP-HPLC on XTerra™ column 3.5 μm (2.1×50 mm), >99% purity at RT=5.38 min using a gradient of 10-90% MeCN (0.1% FA) in water (0.1% FA) over 9 min; >99% purity at RT=5.38 min using a gradient of 10-90% MeOH (0.1% FA) in water (0.1% FA) over 9 min; HRMS m/z calcd. For $C_{37}H_{56}N_{11}O_7$ $[M+H]^+$ 766.4358, found 766.4368.

Compound 8

Aza-lysine compound 8 was synthesized using the same procedure as that described for the synthesis of compound 18 using H-D-Leu-Nle-O-2-chlorotrityl resin, which was prepared from H-Nle-O-2-chlorotrityl resin (0.285 mmol). The crude product was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA) with a flow rate of 10 mL/min and UV detection at 214 nm. The desired fractions were combined and freeze-dried to provide 19 mg (9% yield) of compound 8 as white fluffy solid: analytical RP-HPLC on XTerra™ column 3.5 μm (2.1×50 mm), >99% purity at RT=4.21 min using a gradient of 10-90% MeCN (0.1% FA) in water (0.1% FA) over 9 min; >99% purity at RT=6.22 min using a gradient of 10-90% MeOH (0.1% FA) in water (0.1% FA) over 8 min; HRMS m/z calcd. for $C_{37}H_{56}N_{11}O_7$ $[M+H]^+$ 766.4359, found 766.4371.

Compound 9

Aza-homoserine peptide 9 was synthesized using the same procedure as that described for the synthesis of compound 18 using H-Lys(Boc)-D-Leu-Nle-O-2-chlorotrityl resin, which was prepared from H-Nle-O-2-chlorotrityl resin (0.145 mmol). The crude product was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA) with a flow rate of 10 mL/min and UV detection at 214 nm. The desired fractions were combined and freeze-dried to provide 9 mg (10% yield) of compound 9 as white fluffy solid: analytical RP-HPLC on XTerra™ column 3.5 μm (2.1×50 mm), >99% purity at RT=4.50 min using a gradient of 10-90% MeCN (0.1% FA) in water (0.1% FA) over 9 min; >99% purity at RT=6.77 min using a gradient of 10-90% MeOH (0.1% FA) in water (0.1% FA) over 8 min; HRMS m/z calcd. for $C_{38}H_{58}N_{11}O_7$ $[M+H]^+$ 780.4515, found 780.4522.

Compound 14

Aza-propargylglycine compound 14 was synthesized using the same procedure as that described for the synthesis of compound 18 using H-D-Ser(t-Bu)-Lys(Boc)-D-Leu-Nle-O-2-chlorotrityl resin, which was prepared from H-Nle-O-2-chlorotrityl resin (0.285 mmol). The crude product was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA), with a flow rate of 10 mL/min, and UV detection at 214 nm. The desired fractions were combined and freeze-dried to provide 20 mg (10% yield) of compound 14 as white solid: analytical RP-HPLC on XTerra™ column 3.5 μm (2.1×50 mm), >99% purity at RT=5.12 min using a gradient of 5-50% MeCN (0.1% FA) in water (0.1% FA) over 9 min; >99% purity at RT=7.64 min using a gradient of 5-50% MeOH (0.1% FA) in water (0.1% FA) over 8 min; HRMS m/z calcd. for $C_{36}H_{54}N_9O_7$ [M+H]$^+$ 724.4141, found 724.4157

Compound 15

Aza-iso-tryptophan compound 15 was synthesized using the same procedure as that described for the synthesis of compound 18 using H-His(Tr)-D-Ser(t-Bu)-Lys(Boc)-O-2-chlorotrityl resin, which was prepared from H-Lys(Boc)-O-2-chlorotrityl resin (0.142 mmol). The crude product was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA) with a flow rate of 10 mL/min and UV detection at 214 nm. The desired fractions were combined and freeze-dried to provide 7.5 mg (7% yield) of compound 15 as white solid: analytical RP-HPLC on XTerra™ column 3.5 μm (2.1×50 mm), >99% purity at RT=4.61 min using a gradient of 10-90% MeCN (0.1% FA) in water (0.1% FA) over 9 min; >99% purity at RT=6.74 min using a gradient of 10-90% MeOH (0.1% FA) in water (0.1% FA) over 8 min; HRMS m/z calcd. for $C_{37}H_{56}N_{11}O_7$ [M+H]$^+$ 766.4358, found 766.4372.

Compound 17

Aza-phenylalanine compound 17 was synthesized using the same procedure as that described for the synthesis of compound 18 using H-D-Trp(Boc)-His(Tr)-D-Ser(t-Bu)-Lys(Boc)-O-2-chlorotrityl resin, which was prepared from H-Lys(Boc)-O-2-chlorotrityl resin (0.142 mmol). The crude product was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA), with a flow rate of 10 mL/min, and UV detection at 214 nm. The desired fractions were combined and freeze-dried to provide 7.5 mg (6% yield) of compound 17 as white solid: analytical RP-HPLC on XTerra™ column 3.5 μm (2.1×50 mm), >99% purity at RT=4.36 min using a gradient of 10-90% MeCN (0.1% FA) in water (0.1% FA) over 9 min; >99% purity at RT=6.28 min using a gradient of 10-90% MeOH (0.1% FA) in water (0.1% FA) over 8 min; HRMS m/z calcd. for $C_{40}H_{54}N_{11}O_7$ [M+H]$^+$ 800.4202, found 800.4219.

Compound 19

Aza-phenylalanine peptide 19 was synthesized using the same procedure as that described for the synthesis of compound 18 using H-Nle-O-2-chlorotrityl resin (0.285 mmol). The crude product was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA) with a flow rate of 10 mL/min and UV detection at 214 nm. The desired fractions were combined and freeze-dried to provide 18 mg (10% yield) of compound 19 as white solid: analytical RP-HPLC on XTerra™ column 3.5 μm (2.1×50 mm), >99% purity at RT=5.87 min using a gradient of 10-90% MeCN (0.1% FA) in water (0.1% FA) over 9 min; >99% purity at RT=8.91 min using a gradient of 10-90% MeOH (0.1% FA) in water (0.1% FA) over 14 min; HRMS m/z calcd. for $C_{40}H_{53}N_{11}O_7Na$ [M+Na]+822.4021, found 822.4035.

Compound 20

Aza-4-fluorophenylalanine compound 20 was synthesized using the same procedure as that described for the synthesis of compound 18 using H-Nle-O-2-chlorotrityl resin (0.142 mmol). The crude product was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA) with a flow rate of 10 mL/min and UV detection at 214 nm. The desired fractions were combined and freeze-dried to provide 12.5 mg (13% yield) of compound 20 as white solid: analytical RP-HPLC on XTerra™ column 3.5 μm (2.1×50 mm), >99% purity at RT=4.53 min using a gradient of 10-90% MeCN (0.1% FA) in water (0.1% FA) over 9 min; >99% purity at RT=6.56 min using a gradient of 10-90% MeOH (0.1% FA) in water (0.1% FA) over 8 min; HRMS m/z calcd. for $C_{40}H_{53}N_{11}O_7F$ [M+H]$^+$ 818.4108, found 818.4126.

Compound 13

A solution of compound 14 (3.15 mg, 0.0043 mmol) in 1 mL of MeOH and 0.5 mL of water was treated with TMS-$N_3$ (1.14 μL, 0.0087 mmol), $CuSO_4 \cdot 5H_2O$ (0.27 mg. 0.0011 mmol) and sodium ascorbate (0.43 mg, 0.0022 mmol) and stirred at rt for 14 h. The reaction mixture was concentrated in vacuo and the residue was purified by reverse phase HPLC on a Gemini® C18 column (Phenomenex® Inc., pore size: 110 Å, particle size: 5 μm, 250×21.2 mm) using a binary solvent system consisting of a gradient of 10-60% MeCN (0.1% FA) in water (0.1% FA) with a flow rate of 10 mL/min and UV detection at 214 nm. The desired fractions were combined and freeze-dried to give 2.6 mg (78% yield) of compound 13 as white fluffy solid: analytical RP-HPLC on XTerra™ column 3.5 μm (2.1×50 mm), >99% purity at RT=7.26 min using a gradient of 10-90% MeCN (0.1% FA) in water (0.1% FA) over 8 min; >99% purity at RT=10.66 min using a gradient of 10-90% MeOH (0.1% FA) in water (0.1% FA) over 14 min; HRMS m/z calcd. For $C_{36}H_{55}N_{12}O_7$ [M+H]$^+$ 767.4311, found 767.4324.

Example 1C: Synthesis of Conjugates 40 and 43

Conjugate 40

A solution of compound 19 (8.2 mg. 0.0102 mmol) in 1.5 mL of DMF was treated with NOTA-NHS·TFA·$HPF_6$ [2,2'-(7-(2-((2,5-dioxopyrrolidin-1-yl)oxy)-2-oxoethyl)-1-(2,2,2-trifluoroacetyl)-1,4,7-triazonane-1,4-diyl)diacetic acid-hexafluoro-phosphane, 13.5 mg. 0.0205 mmol] and DIEA (0.011 mL, 0.0615 mmol), and stirred at rt for 14 h. The reaction mixture was concentrated in vacuo and the residue was purified by reverse phase HPLC on a Gemini® C18 column (Phenomenex® Inc., pore size: 110 Å, particle size: 5 μm, 250×21.2 mm) using a binary solvent system consisting of a gradient of 10-60% MeCN (0.1% FA) in water (0.1% FA) with a flow rate of 10 mL/min, and UV detection at 214 nm. The desired fractions were combined and freeze-dried to give 3.1 mg (28% yield) of conjugate 40 as white fluffy solid: analytical RP-HPLC on XTerra™ column 3.5 μm (2.1×50 mm), >99% purity at RT=6.79 min using a gradient of 10-90% MeCN (0.1% FA) in water (0.1% FA) over 8 min; >98% purity at RT=10.02 min using a gradient of 10-90% MeOH (0.1% FA) in water (0.1% FA) over 14 min; HRMS m/z calcd. For $C_{52}H_{73}N_{14}O_{12}$ [M+H]$^+$ 1085.5527, found 1085.5537.

Conjugate 43

A solution of compound 3, (15 mg, formate salt) in 5 mL of water was treated with IN HCl and stirred for 10 min at room temperature. The mixture was freeze-dried (2×) to provide the HCl salt, which was dissolved in 1.0 mL of DMF and treated with 1,4,7-triazacyclononane-1,4-bis-tert-butyl acetate-7-acetic acid (42, 10 mg. 0.0245 mmol), benzotriazol-1-yl-oxytripyrrolidinophosphonium hexafluorophosphate (PyBOP, 0.032 mg. 0.0611 mmol) and DIEA (0.035 mL, 0.2038 mmol), and stirred at rt for 2 h. After complete consumption of compound 3 was observed by LCMS, the volatiles were removed to give an oily residue. The residue was dissolved in DCM (1 mL), treated with 1 mL of a solution of $TFA/TES/H_2O$ (95:2.5:2.5) for 4 h, and concentrated to a residue that was purified by reverse-phase HPLC on a Gemini® C18 column (Phenomenex® Inc., pore size, 110 Å, particle size, 5 μm, 250x21.2 mm) using a gradient of 10-60% MeCN (0.1% FA) in water (0.1% FA) with a flow rate of 6 mL/min and UV detection at 214 nm. The desired fractions were combined and freeze-dried to provide 2.6 mg (13% yield) of conjugate 43 as white fluffy solid: analytical RP-HPLC on Agilent Poroshell column 2.7 μm (4.6x50 mm), >99% purity at RT=6.86 min using a gradient of 10-90% MeCN (0.1% FA) in water (0.1% FA) over 8 min; >99% purity at RT=8.58 min using a gradient of 30-95% MeOH (0.1% FA) in water (0.1% FA) over 14 min; HRMS m/z calcd. For $C_{48}H_{73}N_{14}O_1$ $[M+H]^+$ 1021.5578, found 1021.5572.

Example 1D: Synthesis of Compound 55

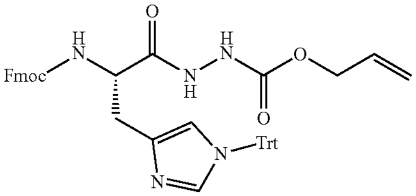

Allyl 2-($N^{\alpha}$-(Fmoc)-$N^{\tau}$-trityl-L-histidyl)hydrazine-1-carboxylate (46) To a solution of Fmoc-His(Trt)-OH (44, 1.0 g. 1.61 mmol, 1 eq.) and Alloc-hydrazine (225 mg, 1.94 mmol, 1.2 eq.) in DMF (25 mL), DIC (0.3 mL, 1.94 mmol, 1.2 eq.) was added, followed by HOBt (262 mg. 1.94 mmol, 1.2 eq.). The mixture was stirred at room temperature for 16 h, quenched with ice-cold water, and extracted with EtOAc (3x100 mL). The combined organic layers were washed twice with cold water and brine, dried over sodium sulfate, filtered, and concentrated under reduced pressure to give a residue that was purified by column chromatography on silica gel using 9:1 DCM/MeOH. Evaporation of the collected fractions gave hydrazide 46 (70%).

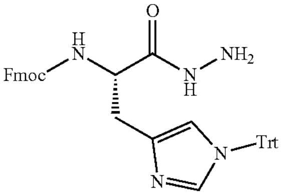

$N^{\alpha}$-(Fmoc)-$N^{\tau}$-trityl-L-histidyl-hydrazide (47) A solution of $Pd_2(dba)_3$ (255 mg, 0.28 mmol) and 1,4-bis(diphenylphosphino)butane (dppb, 119 mg, 0.28 mmol) in THF (40 mL) was stirred for 5 min at room temperature, and transferred to a solution of Fmoc-His(Trt)-NH—NH-Alloc (46, 2 g, 2.79 mmol) and N,N-dimethylbarbituric acid (NDMBA, 4.35 g, 27.86 mmol) in THF (120 mL). The reaction mixture was stirred for 8 h at room temperature. After complete conversion of reactant was confirmed by TLC (starting material at Rf 0.7 disappeared and a new spot was observed at Rf 0.4 eluting twice with 5% MeOH in DCM), the reaction mixture was concentrated under reduced pressure to a residue that was purified by column chromatography on silica gel eluting with 9:1 DCM/MeOH. Evaporation of the collected fractions gave hydrazide 47 (0.96 g, 55%) as off white solid:

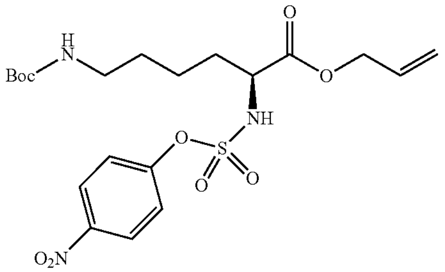 [SMILES: C=CCOC(=O)[C@H](CCCCNC(=O)OC(C)(C)C)NS(=O)(=O)Oc1ccc([N+](=O)[O-])cc1]

Allyl $N^{\varepsilon}$-(tert-butoxycarbonyl)-$N^{\alpha}$-((4-nitrophenoxy) sulfonyl)-L-lysinate (48) A solution of L-H-Lys(Boc)-OAllyl (45, 1.00 g, 3.49 mmol), 4-nitrophenol (1.46 g, 10.48 mmol) and triethylamine (2.91 mL, 20.95 mmol) in dry DCM (30 mL) was added dropwise to a solution of 4-nitrophenyl chlorosulfate (1.66 g, 6.98 mmol) in dry DCM (6 mL) at −78° C. under argon. After stirring at −78° C. for 2 h, complete conversion was observed by TLC (free amine appeared at Rf 0.1 and was $KMnO_4$ and ninhydrin active and a new spot was observed around Rf 0.5 in 50% EtOAc in hexanes). The cooling bath was removed. The mixture warmed to room temperature. The reaction mixture was diluted with DCM (100 mL) and washed with 5% citric acid solution (100 mLx3), dried over sodium sulfate, filtered, and concentrated under reduced pressure to a residue that was purified by column chromatography on silica gel using 1:1 hexanes/EtOAc as eluent. Evaporation of the collected fractions gave sulfamidate 48 (1.00 g, 58%) as pale-yellow solid.

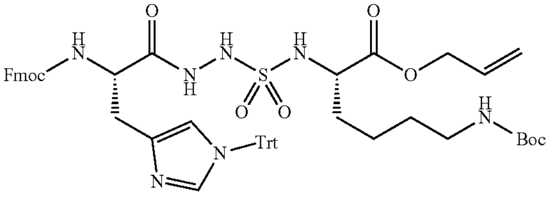

Fmoc-L-His(Trt)-azasulfurylglycinyl-L-Lys(Boc)-OAllyl (49) A solution of sulfamidate 48 (500 mg, 1.026 mmol) in MeCN (10 mL) was treated with Fmoc-L-His(Trt) hydrazide 47 (617 mg, 0.974 mmol) and concentrated under reduced pressure to a residue. The residue was dissolved in MeCN (10 mL) and transferred into a microwave vial. The vessel was sealed and heated to 60° C. using microwave irradiation for 2.5 h. The vessel was cooled to room temperature and opened. The volatiles were evaporated under reduced pressure and the residue was purified by column chromatography on silica gel eluting with 1:4 hexanes/EtOAc as eluent. Evaporation of the collected fractions gave azasulfuryl tripeptide 49 (409 mg, 43%) as white solid.

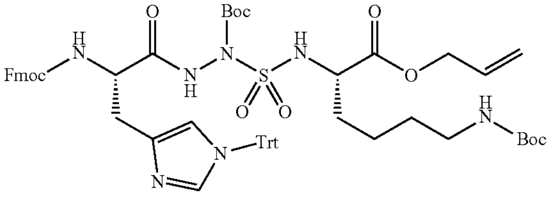

Fmoc-L-His(Trt)-azasulfurylglycinyl(Boc)-L-Lys(Boc)-OAllyl (50) A solution of azasulfuryl-glycine tripeptide 49 (400 mg g, 0.41 mmol) in MeCN (20 mL) was treated with DMAP (10 mg, 0.08 mmol) followed by a solution of di-tert-butyl dicarbonate (89 mg, 0.41 mmol) in MeCN (2 mL). The reaction mixture was stirred at room temperature for 30 min. Complete conversion was confirmed by TLC (starting material Rf 0.5 disappeared, and a new spot was observed at Rf 0.8 in 70% EtOAc in hexanes). The reaction mixture was diluted with EtOAc (50 mL), washed with saturated $NH_4Cl$ and brine, dried over sodium sulfate, filtered, and concentrated under reduced pressure to a residue that was purified by column chromatography on silica gel eluting with 1:4 hexanes/EtOAc as eluent. Evaporation of the collected fractions gave Boc protected azasulfurylglycinyl tripeptide 50 (390 mg, 97%) as off-white solid.

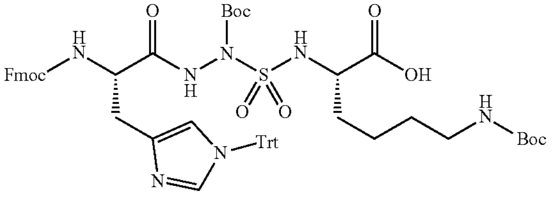

Fmoc-L-His(Trt)-azasulfurylglycinyl(Boc)-L-Lys(Boc)-OH (51) A solution of $Pd_2(dba)_3$ (31.3 mg, 0.03 mmol) and 1,4-bis(diphenylphosphino)butane (dppb) (14.6 mg, 0.03 mmol) in THF (10 mL) was stirred for 5 min at room temperature, and transferred to a solution of Boc tripeptide 50 (370 mg. 0.34 mmol) and N,N-dimethylbarbiturate (NDMBA, 534 mg, 3.42 mmol) in THF (30 mL). The reaction mixture was stirred for 2 h at room temperature. After complete conversion was observed by TLC (starting material Rf 0.7 disappeared and a new spot was observed at Rf 0.15 in 70% EtOAc in hexanes), the reaction mixture was concentrated under reduced pressure to a residue that was dissolved in MeCN (10 mL) and filtered. The filtrate was concentrated to dryness. The yellow residue was used in the next step without further purification.

Compound 55

Azasulfuryl peptide 55 was synthesized starting from H-D-Leu-Nle-O-2-chlorotrityl resin 52, which was prepared from H-Nle-O-2-chlorotrityl resin (0.14 mmol) according to the previously described protocol. Azasulfuryl tripeptide 51 (1.2 equiv) was coupled to the resin-bound peptide sequence using DIC (3.0 equiv) and HOBt (3.0 equiv) at rt overnight. A resin aliquot was cleaved as described earlier using TFA/TES/$H_2O$ (95:2.5:2.5) and analyzed by LC-MS, which indicated Fmoc-His-AsG-Lys-D-Leu-Nle-OH was of approximately 70% purity: RT 7.27 min on an Agilent Poroshell reverse-phase column using a gradient of 10-90% MeCN (0.1% FA) in water (0.1% FA) over 14 min. After the peptide was elongated and the Fmoc group removed, the side chain protected linear sequence 54 was cleaved from the resin using a cocktail of 1:1:3 AcOH:TFE:DCM. Macrocyclization was performed in solution on aza-sulfuryl peptide using EDC·HCl (3 equiv) and HOBt (3 equiv) in acetonitrile (0.001 M) to yield side chain protected aza-sulfuryl cyclopeptide, which was confirmed by LCMS analysis: RT 9.27 min on an Agilent Poroshell reverse-phase column using a gradient of 10-90% MeCN (0.1% FA) in water (0.1% FA) over 14 min. After removal of side chain protection with a 50% solution of TFA:TES:$H_2O$ (95:2.5:2.5) in DCM, the cyclic peptide was purified by reverse-phase HPLC on a Gemini® C18 column (Phenomenex® Inc., pore size, 110 Å, particle size, 5 μm, 250×21.2 mm) using a gradient of 10-60% MeCN (0.1% FA) in water (0.1% FA) with a flow rate of 10 mL/min and UV detection at 214 nm. The desired fractions were combined and freeze-dried to provide 7.1 mg (6.6% yield) of [$AsG^2$]-CP-2 (55) as white fluffy solid: analytical RP-HPLC on Agilent Poroshell column 2.7 μm (4.6×50 mm), >99% purity at RT=6.65 min using a gradient of 10-90% MeCN (0.1% FA) in water (0.1% FA) over 8 min; >99% purity at RT=7.55 min using a gradient of 30-95% MeOH (0.1% FA) in water (0.1% FA) over 8 min; HRMS m/z calcd. for $C_{35}H_{54}N_{11}O_7S$ $[M+H]^+$ 772.3923, found 772.3921 and $C_{35}H_{53}N_{11}O_7SNa$ $[M+N^{\alpha}]^+$ 794.3742, found 794.3738.

Example 2: Anti-Amyloidogenic and Neuroprotective Activity of Cyclic Peptide Mimetics Amyloid generation can be identified and quantified using the thioflavin T (ThT) fluorescence dye assay. A benzothiazole salt, ThT binds to amyloid fibrils, and on binding, exhibits enhanced fluorescence in the emission spectrum. Agents that bind and inhibit aggregation of Aβ diminish ThT fluorescence relative to untreated Aβ. The extent of Aβ40 aggregation in the presence of increasing concentrations of azacyclopeptides and azasulfurylcyclopeptide 55 was evaluated by the ThT assay. Fluorescence of Aβ40 that was aged for 48 h was used as control, defined as 0% anti-amyloidogenic activity, and compared with fluorescence in the presence of cyclic peptide mimics at increasing concentrations to measure anti-amyloidogenic activity. To facilitate head-to-head comparisons, azacyclopeptides are grouped into four families: a) Compounds 2-7, each having an aza-glycine in a different position; b) azacyclopeptides with aza-residues other than azaGly, compounds 8-20; c) NOTA-cyclic peptide mimic conjugates (40 and 43) and d) azasulfurylcyclopeptide (55).

a) Compounds 2-7. In the ThT assay, analogs with azaGly residues at the 6-, 5- and 3-positions respectively (e.g., 2, 3 and 5) demonstrated significantly higher activity than compound 1 to inhibit Aβ aggregation at 1:1 Aβ:azaGly-cyclopeptide ratios (Table 3). At this Aβ:azacyclopeptide ratio, compound 4 was slightly better and compounds 6 and 7 were slightly less active than compound 1 at inhibiting Aβ aggregation. Incubation of azaGly analogs 3, 5, 6 and 7 with Aβ dramatically prolonged the lag phase and reduced the ThT fluorescence, suggesting that these analogs interact with early Aβ species and most likely inhibit amyloid elongation. Similarly, at and below stoichiometric concentrations, compound 2 prolonged dramatically the lag-phase and reduced ThT fluorescence, but above stoichiometric concentrations, compound 2 promoted significantly fibrilization of Aβ shortening the lag-phase and increasing ThT fluorescence. At such high concentrations, compound 2 may serve to promote nucleation and seed Aβ aggregation. Compound 5 exhibited significant activity. The tolerance of replacement of certain of the original amino acids of compound 1 by azaGly with respect to inhibitory activity on Aβ aggregation is likely due to the effect of the additional hydrogen-bond donor which may favor interactions that compensate for the loss of more hydrophobic side chains.

Considering that self-assembly and aggregation of Aβ are key components of AD pathogenesis, the ability of azaGly-cyclopeptides 2-7 to reduce Aβ-induced toxicity was next tested in rat pheochromocytoma PC12 cells. Cells were incubated for 24 h with Aβ40 (10 μM) that had been aged for 48 h in the presence and absence of increasing concentrations of the azacyclopeptides. Cell viability was assessed using the 3-(4,5-dimethylthiazol-2-yl)-2,5-diphenyltetrazolium bromide (MTT) survival assay (Table 2). In this assay, viable cells reduce permeable MTT by active metabolism to produce a purple-colored formazan product with absorbance maximum near 570 nm. Dead cells lose the ability to convert MTT into formazan. The quantity of formazan is therefore directly proportional to the number of viable cells and measurable over time by recording changes in absorbance using a spectrophotometer. Neurons are susceptible to the lethal effects of misfolded proteins which are likely to aggregate at increased concentration. The pheochromocytoma (PC12) cell line is commonly used in in vitro studies to examine neuronal variation and neurotoxicity as a model of neurodegenerative disease. The results of the inhibition of amyloidogenic activity in vitro using the ThT model and MTT cell survival model, comparing Aβ control and compound 1 versus compounds 2-7 are shown in Table 3 below.

TABLE 3

Anti-amyloidogenic activity of compound 1 versus compounds 2-7.

| | Inhibition of amyloidogenic activity (%)[a] | | | | Cells survival (%)[b] | |
|---|---|---|---|---|---|---|
| Compound | 1:10 | 1:5 | 1:1 | 1:0.1 | 1:5 | 1:1 |
| Aβ | 0 | 0 | 0 | 0 | 67.6 | |
| 1 | 92.8 | 84.7 | 44.6 | — | 87.9 | 70.225 |
| 2 | — | — | 76.7 | 63.9 | 57.6 | 65.0 |
| 3 | 83.7 | 81.3 | 83.7 | — | 93.4 | 88.9 |
| 4 | 68.8 | 75 | 50.2 | — | 74 | 62.2 |
| 5 | 90.8 | 91.1 | 89.8 | 55.3 | 67.5 | 65.6 |
| 6 | 81.8 | 80.1 | 38.0 | — | 72.6 | 63.5 |
| 7 | 80.5 | 78.8 | 40.1 | — | 81 | 64.730 |

[a]Inhibition of amyloidogenic activity was determined by the ThT method using 10 μM of soluble Aβ40 at the indicated Aβ:peptide ratios.
[b]Effect of compound 1 and azaGly peptides on Aβ-induced toxicity. Aβ40 (20 μM) was aged for 48 h without or with azaGly peptides at Aβ:peptide ratios of 1:5 and 1:1 and incubated with PC-12 cells for further 24 h. Cell survival was then determined by the MTT assay.

Despite the superior activity to inhibit Aβ aggregation that was exhibited by compounds 2 and 5 compared to that of compound 1, both were unable to enhance cell viability at Aβ:peptide ratios 1:1 and 1:5. However, significant cytoprotecting activity was observed for compound 2 at lower Aβ:peptide ratios. At Aβ:peptide ratio of 1:0.1. 2 increased the cell survival to 87% compared to 68% for Aβ. Among the azaGly-cyclopeptides, only compound 3 demonstrated significantly higher neuroprotective activity than compound 1. Incubation of compound 3 with Aβ at 5:1 ratio reversed almost completely Aβ toxicity to the cells. In contrast to inhibitory activity on amyloidogenesis, which exhibited tolerance to replacing azaGly for L- and D-residues in compound 1, the influences of such substitutions on cell viability were generally detrimental to activity except in the case of substitution of D-Ser by azaGly, which improved cell survival.

b) Azacyclopeptides with aza-residues other than azaGly (8-20). Replacement of residues at the 4- and 5-positions of compound 1 with aza-counterparts in compounds 15 and 16 gave analogs exhibiting superior anti-amyloidogenic activity in the ThT assay than compound 1 at 1:1 Aβ:azacyclopeptide ratios. Substitutions of aza-residues at the 6- and 4-positions in compounds 8 and 13 gave azacyclopeptides with slightly better anti-amyloidogenic activity at the 1:1 ratio. On the other hand, replacement of D-Ser in the 5-position and D-Leu in the 1-position with corresponding aza-residues in compounds 9 and 18 diminished significantly anti-amyloidogenic activity in the ThT binding assay.

The neuroprotective and anti-amyloidogenic activities of compound 16, both were superior to those of compound 1. Moreover, moderately better inhibitors of Aβ aggregation 8 and 13 exhibited net improvements in neuroprotective activity relative to compound 1. As previously noted, examining certain azaGly cyclopeptides above, the capacity for the aza-counterparts to exhibit neuroprotection did not always correlate with ability to inhibit Aβ aggregation. Specially, compound 15 exhibited a modest improvement in neuroprotective activity, in spite showing notable improvement over compound 1 in inhibiting Aβ aggregation at a 1:1 Aβ:azacyclopeptide ratio. Furthermore, compounds 9 and 18 demonstrated respectively significantly better and similar neuroprotective activity compared to compound 1 in spite their lower anti-amyloidogenic activities in the ThT assay. The results of the inhibition of amyloidogenic activity in vitro using the ThT model and MTT cell survival model, comparing Aβ control and compound 1 versus the azacyclopeptide compounds addressed above are shown in Table 4 below.

TABLE 4

Anti-amyloidogenic activity of compound 1 versus azacyclopeptides

| | Inhibition of amyloidogenic activity | | | Cells survival (%) | |
|---|---|---|---|---|---|
| Compound | 1:10 | 1:5 | 1:1 | 1:5 | 1:1 |
| Aβ | 0 | 0 | 0 | 64.8 | |
| 1 | 92.8 | 84.7 | 44.6 | 87.9 | 70.2 |
| 8 | 80.9 | 77.8 | 54.4 | 91.3 | 80.1 |
| 9 | 77.2 | 77.9 | 8.3 | 97.9 | 82.8 |
| 13 | 78.4 | 72.6 | 58.0 | 96.3 | 70.8 |
| 15 | 86.1 | 81.6 | 78.0 | 71.7 | 78.8 |
| 16 | 85.1 | 76.4 | 72.9 | 94.5 | 86.3 |
| 18 | 37.5 | 17.1 | 15.4 | 76.3 | 72.8 |

Another set of azacyclopeptides was synthesized and evaluated. In general, these azacyclopeptides possessed aromatic residue side chains (e.g., azaPhe), which at the 5-, 4- and 1-positions (e.g., compounds 10, 11, 17, 19 and 20) caused reduced activity in inhibiting Aβ aggregation relative to compound 1. At the $His^4$ position, however, azaPra and azaPhe residues, compounds 12 and 14 respectively, improved anti-amyloidogenic activity at a 1:1 Aβ:azacyclopeptide ratio. Except in the case of compound 17, azacyclopeptide compounds 10-12, 14, 19 and 20, all exhibited similar neuroprotective activity as compound 1 despite their ability to inhibit Aβ aggregation, further demonstrating a limited correlation between these activities. 25 c) NOTA-cyclic peptide conjugates (40 and 43). Certain aza-analogs (compounds 3 and 19) and compound 1 were labeled with NOTA, which is a preferred chelator of $^{64}$Cu that has been used to prepare conjugates for PET studies. In the ThT and cell survival assays, the anti-amyloidogenic and neuroprotective activities were tested for the resulting NOTA-azacyclopeptide conjugates: conjugate 40, conjugate 43, and 1-NOTA. Attachment of NOTA to compound 1 and 19 in 1-NOTA and 40 increased significantly anti-amyloidogenic activity. Neuroprotective of activities 1-NOTA and 43 were improved relative to the parent peptides. A 5-folds excess of conjugates 1-NOTA and 43 completely reversed the pathological effect of Aβ. On the other hand, attachment of NOTA reduced the anti-amyloidogenic activity of 3.

d) Azasulfurylglycine cyclic peptide compound 55. Considering the high in vitro activity of compound 3, the AzaGly at position 5 was replaced with azasulfurylglycine. In the ThT and cell survival assays, Compound 55 demonstrated superior anti-Aβ aggregation activity compared to compound 1 at 1:1 Aβ:55 ratio and comparable cytoprotecting activity compared to compound 3.

TABLE 5

Anti-amyloidogenic activity of compound 1 versus azacyclopeptides, NOTA conjugates, and azasulfuryl compound.

| | Inhibition of amyloidogenic activity(%)[a] | | | Cells survival (%)[b] | |
|---|---|---|---|---|---|
| Compound | 1:10 | 1:5 | 1:1 | 1:5 | 1:1 |
| Aβ | 0 | 0 | 0 | 64.8 | |
| 1 | 92.8 | 84.7 | 44.6 | 87.9 | 70.2 |
| 10 | 86.2 | 85.2 | 8.2 | 83.4 | 75.4 |
| 11 | 54.2 | 54.7 | 3.5 | 74.3 | 72.4 |
| 12 | 80.9 | 77.7 | 54.4 | 87.9 | 70.1 |
| 14 | 81.4 | 81.2 | 76.9 | 83.5 | 71.7 |
| 17 | 79.8 | 36.9 | 3.5 | 69.5 | 61.8 |
| 19 | 61.2 | 54.5 | 12.5 | 74.5 | 73.0 |
| 20 | 68.4 | 48.4 | 1.6 | 84.9 | 73.0 |
| NOTA analogs | | | | | |
| 1-NOTA | | 93.2 | 91.4 | 95.9 | 82.7 |
| Conjugate 40 | 60.0 | 49.7 | 49.5 | 47.6 | 66.9 |
| Conjugate 43 | — | 74.1 | 28.3 | 103.5 | 68.1 |
| Azasulfurylglycine cyclic | | | | | |
| 55 | | 73 | 68.5 | 106 | 76.9 |

Example 3: In Vivo Activity of Conjugates $^{64}$Cu-labeling

1-NOTA was radiolabeled with $^{64}Cu(OAc)_2$ at 40° C. for 30 min with yields superior to 95%. A significant aggregation of the peptide was evident even before the labeling. Conjugates 40 and 43 were successfully radiolabeled with $^{64}Cu(OAc)_2$ at room temperature for 15 min with yields superior to 95%. The apparent molar activities measured were 66 to 72 Tera Becquerel per millimole (TBq/mmol) for the three $^{64}$Cu/NOTA-conjugates.

PET Imaging and Biodistribution Studies in Balb/c Mice

Different formulations were tested with the $^{64}$Cu-1-NOTA conjugate to investigate the solubility of the PET tracer in vivo and select the best formulation for PET imaging studies. Saline was attempted but better solubilization of $^{64}$Cu-1-NOTA was achieved using 4% bovine serum albumin and 9% sucrose in saline 0.9%. Intra-lipid (20% IV fat-emulsion) formulations showed lower uptake in the lungs and a higher uptake in the gastrointestinal tract and gallbladder. High lung and liver uptake were also found for $^{64}$Cu-1-NOTA formulated in 8% DMSO. For further in vivo studies, 8% DMSO and 9% sucrose (for azaconjugates) were used. All three $^{64}$Cu-conjugates ($^{64}$Cu-40, $^{64}$Cu-43 and (4Cu-1-NOTA) exhibited similar brain to kidney and brain to liver ratios.

FIG. 1 shows formulation in 9% sucrose in saline. The uptake of stable $^{64}$Cu-conjugate 43 into the thalamus of Tg female 5×FAD AD mice increased with age from 44 to 72 days paralleling Aβ oligomer formation (FIG. 1A-B). Images were taken 3 weeks apart on the same 5×FAD mouse for $^{64}$Cu-conjugate 43 and $^{11}$C-PIB (FIGS. 1B and C) using the 2-(4'-[$^{11}$C]methylaminophenyl)-6-hydroxybenzothiazole ($^{11}$C-PIB) compound. Use of $^{11}$C-PIB is limited to 1 h due to short half-life ($t_{1/2}$=20.4 min). Uptakes of $^{11}$C-PIB and $^{64}$Cu-conjugate 43 appear at different regions with superior contrast for $^{64}$Cu-conjugate 43 likely because $^{11}$C-PIB targets mainly fibrils and insoluble plaques and $^{64}$Cu-conjugate 43 targets Aβ oligomer, suggesting specific binding of $^{64}$Cu-conjugate 43. In control 44 day-old WT mouse at 1-day post-injection of $^{64}$Cu-conjugate 43, brain uptake is very low (FIG. 1D). Non-transgenic littermates (labeled as wild type (WT) controls in the text and FIG. 1D) were housed in the same manner as 5×FAD mice and used for comparison.

Figure 1E:
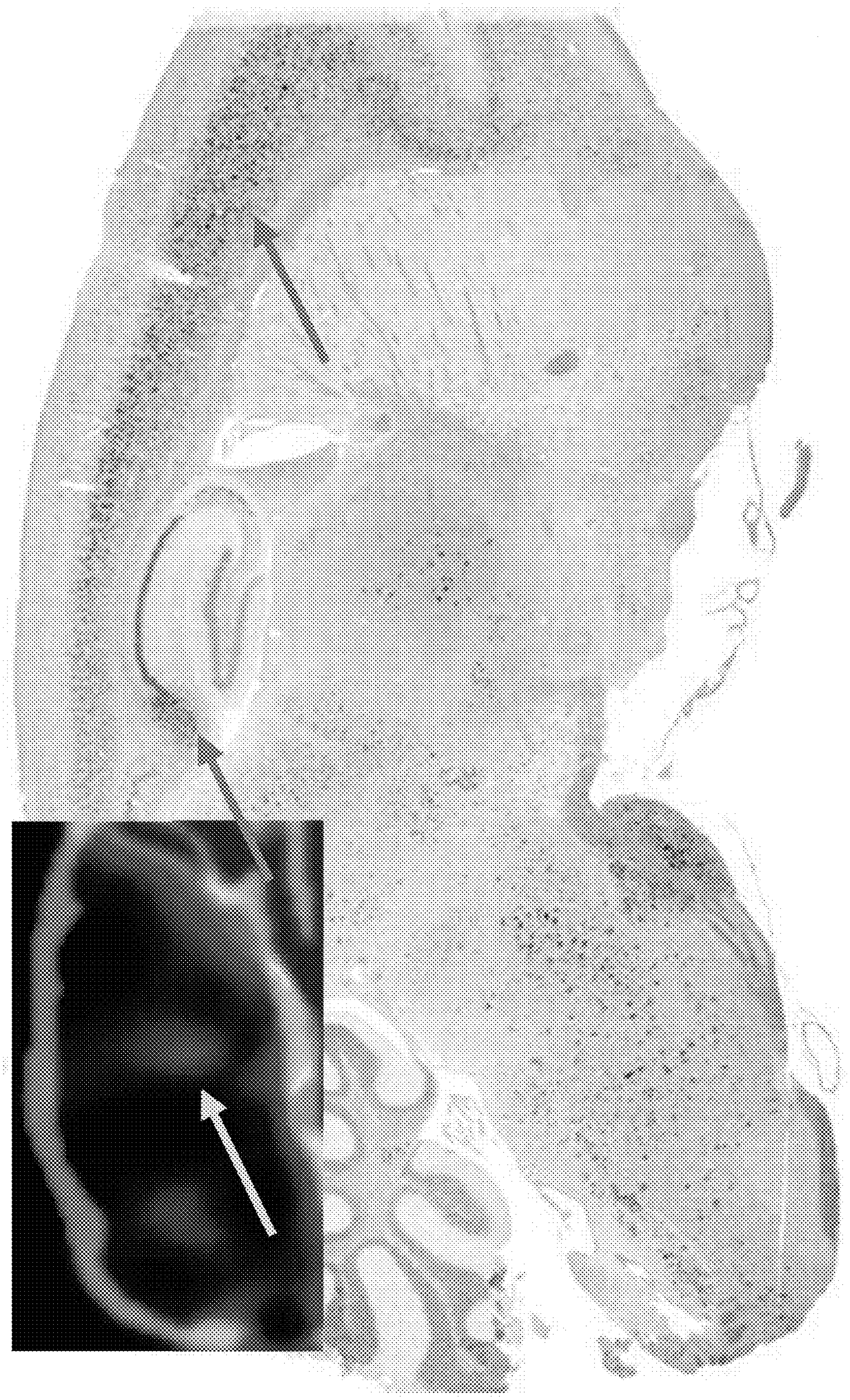
FIG. 1E shows ex vivo immunohistochemistry (IHC) with mouse anti-AB 1-16 antibody confirming the presence of Aβ species in thalamus (yellow arrow) and a PET brain image with $^{64}$Cu-conjugate 43 from the same Tg mouse is displayed above IHC image

FIG. 1E shows ex vivo Immunohistochemistry (IHC) with mouse-anti-Aβ 1-16 antibody confirmed high levels of Aβ in thalamus of 58-day old 5×FAD mice slice (FIG. 1E). Cortical and subiculum staining (blue arrows) were also seen with the mouse-anti-Aβ 1-16 antibody, which targets high order of Aβ species like fibrils and plaques present in 2-month old 5×FAD.

Amyloid plaque detection was evaluated in 4.5-7-month-old Tg [5×FAD] mice and age-matched wild-type controls using the $^{11}$C-PIB compound. 5×FAD mice carry both mutant human APP(695) with the Swedish (K670N, M671L), Florida (1716V), and London (V717I) Familial Alzheimer's Disease (FAD) mutations and human PS1 harboring two FAD mutations, M146L and L286V. 5×FAD mice develop plaque formation beginning at 2 months and cognitive deficits at 4-6 months. Signs of amyloid beta can be detected in hippocampus with 6Cu-conjugate 40 at 4.5 month using PET imaging, as shown in FIG. 1A. Imaging of $^{64}$Cu-conjugate 40 in 5×FAD mice showed an increasing accumulation of activity in the Aβ species moving from 0.165±0.005 injected dose per gram of tissue (% ID/g) at 4.5 months (FIG. 1A) to 2.102±0.059% ID/g at 6 months (FIG. 1B). Amyloid beta of $^{64}$Cu-conjugate 40 in hippocampus at 1 h post injection (1.285±0.034% ID/g) was similar to that of $^{11}$C-PIB (1.038±0.028% ID/g. FIG. 1) in the cortex. Imaging of $^{64}$Cu-conjugate 40 in 5×FAD mice showed the highest activity value in Aβ species at 1 day post injection.

Figures 2A, 2B, 2C:
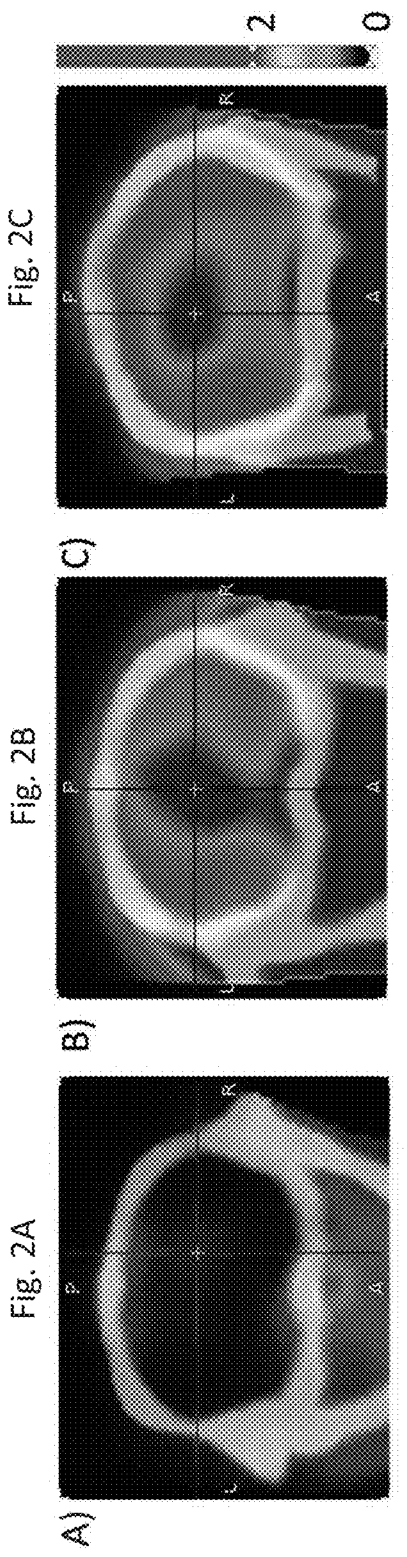
FIGS. 2A, 2B, and 2C show examples of head transaxial PET images of 6-month-old 5×FAD mice administered (A) $^{64}$Cu-1-NOTA (B) $^{64}$Cu-conjugate 40 and (C) $^{64}$Cu-conjugate 43 at 20 h post-injection.

FIG. 2 shows examples of head transaxial PET images of 6-month old 5×FAD mice administered (A) $^{64}$Cu-1-NOTA (B) $^{64}$Cu-conjugate 40 and (C) $^{64}$Cu-conjugate 43 at 20 h post-injection.

Both $^{64}$Cu-conjugate 40 (2.102±0.059% ID/g) and $^{64}$Cu-conjugate 43 (2.030±0.056% ID/g) showed similar Aβ uptakes, which were approximatively five times superior to that of $^{64}$Cu-1-NOTA (0.430±0.010% ID/g) in 6-month old 5×FAD mice.

Figures 2D, 2E, 2F:
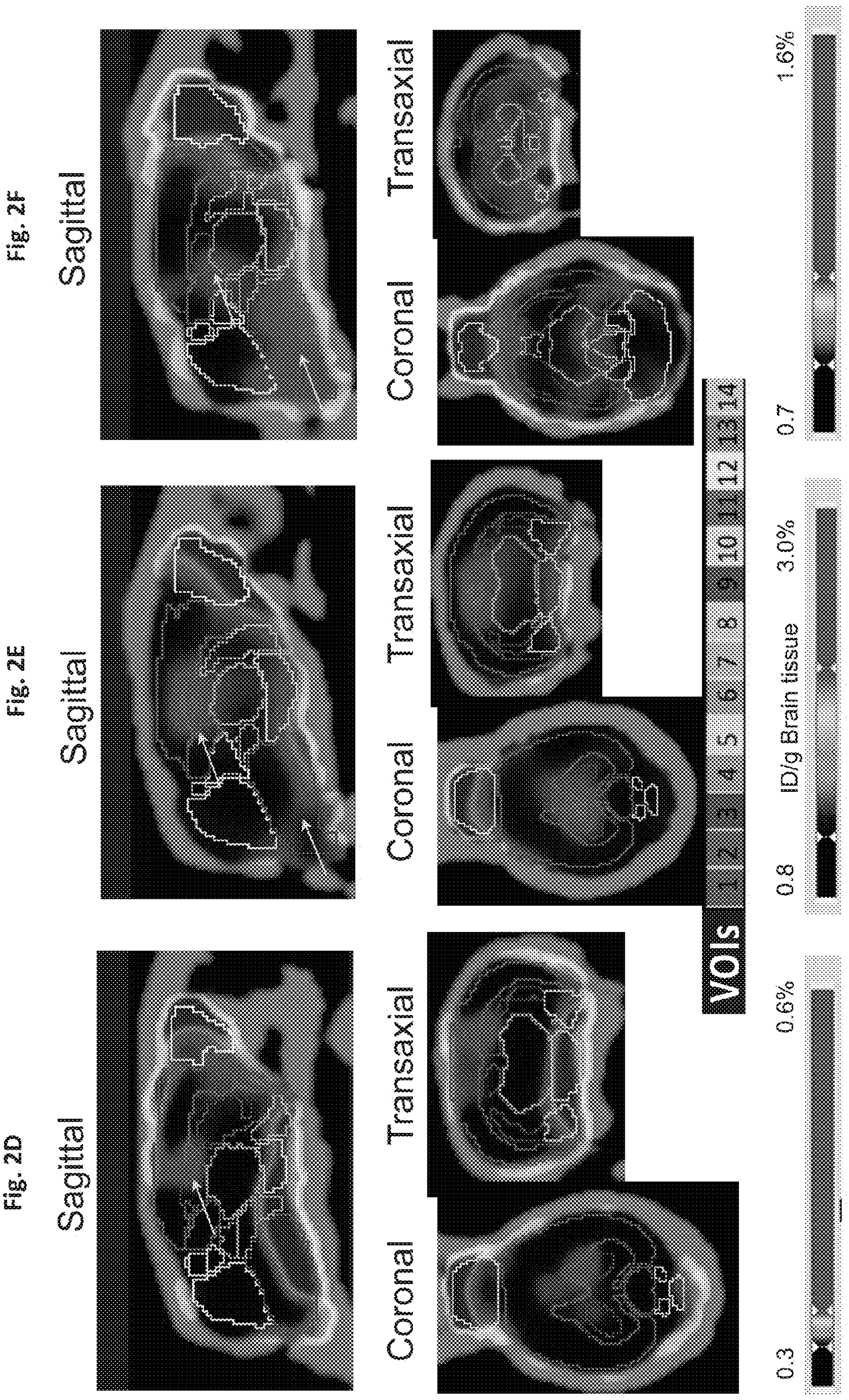
FIGS. 2D and 2E show representative fused PET-CT images at 1-day post-injection of $^{64}$Cu-1-NOTA (2D) and of $^{64}$Cu-conjugate 43 (2E) into 6-month-old 5×FAD mice.
FIG. 2F shows PET-CT images of 7-month-old 5×FAD mice at 40 min post-injection of $^{11}C$-PIB.

FIG. 2D shows a representative fused PET-CT image at 1-day post-injection of $^{64}$Cu-1-NOTA and 2E shows a representing fused PET-CT image at 1-day post-injection of conjugate $^{64}$Cu-43 into 6-month-old 5×FAD mice. FIG. 2F shows PET-CT images of 7-month-old 5×FAD mice at 40 min post-injection of $^{11}$C-PIB. Red and blue colours represent respectively highest and zero uptake. Arrow shows amyloid beta species in brain. Different intensity scales were used for PET images. In 5×FAD mice, tracer $^{64}$Cu-43 exhibited the Aβ amyloid uptake value in hippocampus at day 1 post injection. Images were taken 3 weeks apart on different mouse for $^{64}$Cu-43 and $^{11}$C-PIB. Co-registration of experimental image data with brain mask to mouse atlas space was achieved to identify volumes of interest. 1. Striatum; 2. Cortex; 3. Hippocampus; 4. Thalamus; 5. Cerebellum; 6. Basal forebrain septum; 7. Hypothalamus; 8. Amygdala; 9. Brain stem; 10. Central gray; 11. Superior Collicili; 12. Olfactory bulb; 13. Midbrain; 14. Inferior colliculi.

It has been shown that cyclic peptide mimetics comprising aza-amino acids exhibited anti-amyloidogenic and neuroprotective activity against Aβ. In particular, aza-cyclopeptide compounds 3, 8, 9, 13, 16 showed enhanced neuroprotective activity relative to compound 1. Similarly, azasulfurylglycine derivative compound 55 demonstrated superior anti-amyloidogenic and neuroprotective activities compared to compound 1. In vivo studies showed the potential of 6Cu-NOTA-conjugates 40 and 43 to allow visualization of amyloid beta oligomer using PET imaging indicating potential to serve as tracers for amyloid beta oligomer detection, especially at early stages of amyloid beta oligomer development

Example 4A: In Vivo Activity of Compounds on Longevity in *C. elegans*

Figure 3A:
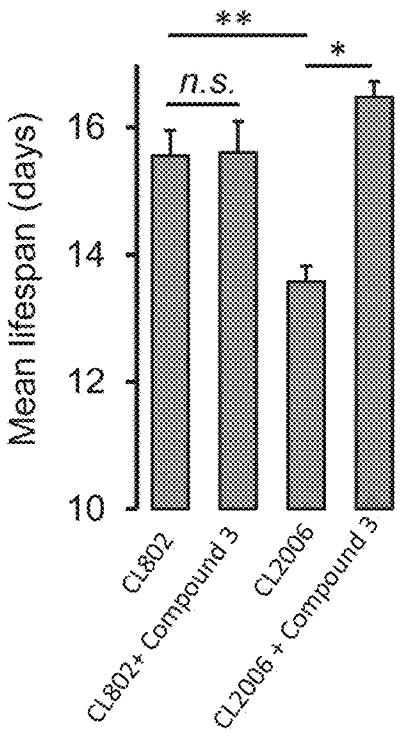
FIG. 3 shows graphs displaying results of studies performed in various strains of *C. elegans* testing effect on lifespan (3A), activity in terms of thrashes per minute (3B,) and chemotaxis index (3C) after either treatment with a compound 3 or non-treatment.

Compound 3 was used in two in vivo transgenic *Caenorhabditis* (C.) *elegans* models expressing human Aβ42. The CL2006 *C. elegans* strain produces constitutively a body-wall muscle-specific Aβ42, the aggregation of which causes age-dependent paralysis, motility dysfunction and consequently short lifespan. The CL2355 strain expresses a temperature-inducible pan-neuronal Aβ42, accumulation of which leads to deficits in chemotaxis, associative learning and thrashing in liquid. The CL2006 mutant and control CL802 wild type worms had respective lifespans of 13.6 and 15.6 days (P<0.005, FIG. 3A). Treatment of CL2006 worms with compound 3 (50 μM) increased (p<0.005) lifespan to that of wild type and negated the effect of overexpressed Aβ. Compound 3 had no toxicity and no influence on wild type CL802 worm longevity.

Example 4B: In Vivo Activity of Compounds on Motility in *C. elegans*

Figure 3B:
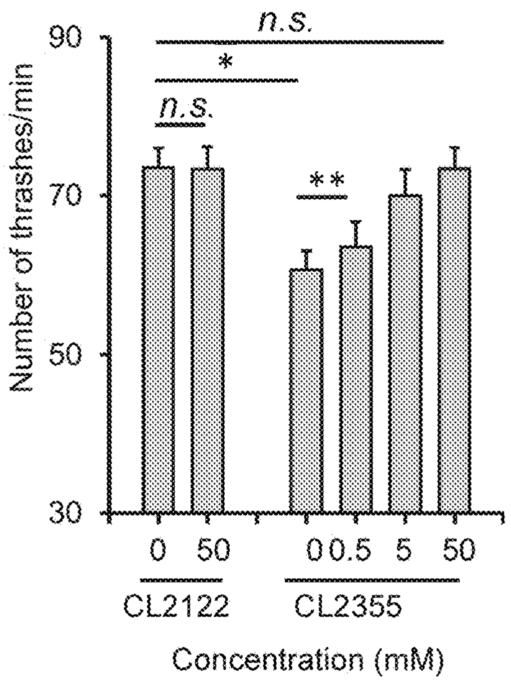
Figure 3C:
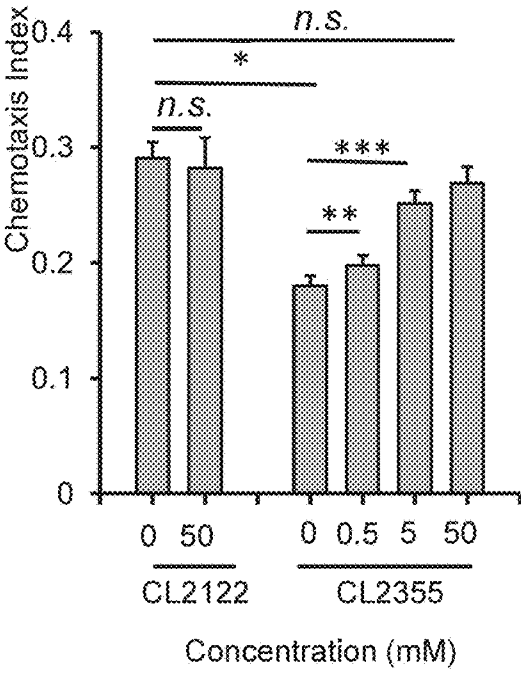

Temperature-sensitive CL2355 mutants and wild type CL2122 worms bend respectively about 61 and 73 times per minute at elevated temperature (23° C.) due to former suffering from Aβ induced toxicity (P<0.005, FIG. 3B). Transgenic CL2355 and control CL2122 worms were fed increasing concentrations of compound 3 at 16° C. for 36 h and then at 23° C. for another 36 h, before the number of thrashes were counted for 1 min. Data are plotted as a mean±SD from three experiments (n=20, each; *p<0.0005 vs. untreated CL2122 worms, **p<0.005 vs. untreated CL2355 worms, n.s.=not significant). Chemotaxis behavior of neuronal Aβ-expressing strain *C. elegans* CL2355 and transgenic control strain CL2122 was determined in the absence or presence of compound 3. Worms were fed increasing concentrations of compound 3 at 16° C. for 36 h and then at 23° C. for another 36 h. At the end of the incubation time, the animals were placed in the center of an assay plate (100×15 mm) containing 1 μL of attractant (0.1% benzaldehyde in ethanol) and 1 μL of 1 M sodium azide at two opposite edges of the plate, and 1 μL of increasing concentration of compound 3 together with 1 μL of 1 M sodium azide on the remaining opposite edges of the plate. Chemotactic index (CI) was then determined after 1 h incubation at room temperature, using the formula: CI=(number of worms at attractant sites-number of worms at control sites)/total number of worms. Results are depicted in FIG. 3C as mean±SD from three independent experiments (n=20 each; *p<0.0005 vs. CL2122 worms, p<0.05 vs. untreated CL2355 strain, *p<0.0005 vs. untreated CL2355 strain, n.s.=not significant).

The motility of CL2355 mutants increased dose dependently to untreated wild type CL2122 levels upon feeding with increasing concentrations of compound 3 (P<0.005, FIG. 3B). No effect on bending frequency was observed on treatment of wild type CL2122 worms with compound 3. In the chemotaxis assay, the chemotaxis indexes (CI) of the control strain CL2122 and transgenic strain CL2355 were respectively 0.29±0.01 and 0.18±0.01, suggesting that the transgenic CL2355 are neuronally impaired. Treatment of CL2355 mutants with compound 3 dose dependently increased CI levels to that of the wild type and neutralized the damaging effect of aggregated Aβ. Treatment of wild type CL2122 worms even with highest amount of compound 3 did not change the CI levels (FIG. 3C). As shown, compound 3 can neutralize the effect of aggregated Aβ in *C. elegans* models, indicating that azapeptides described herein have potential for use in treating pathologies in animals in which aggregated Aβ can play a role.

According to some embodiments, disclosed is a cyclic peptide mimetic having the structure c($X^1$-$X^2$-$X^3$-$X^4$-$X^5$-$X^6$) wherein: each of $X^1$, $X^2$, $X^3$, $X^4$, $X^5$, and $X^6$ is either an L-amino acid residue, a D-amino acid residue, or $X^7$; and wherein one of $X^1$, $X^2$, $X^3$, $X^4$, $X^5$, and $X^6$ is defined as $X^1$; and wherein the remaining $X^1$, $X^2$, $X^3$, $X^4$, $X^5$, and $X^6$ which are not defined as $X^7$ are amino acid residues in alternating L-configuration and D-configuration; wherein $X^7$ is an aza-amino acid residue or azasulfuryl-amino acid residue having the structure:

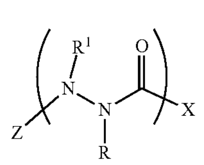

or

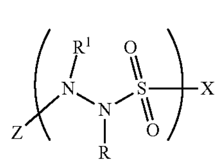

wherein the R group is the same R group as defined in naturally occurring and synthetic amino acids; $R^1$ is hydrogen, alkyl, aryl, heteroalkyl, heteroaryl, aryl alkyl or heteroaryl alkyl, or $R^1$ and R could together form a cyclic ring; Z is a carbonyl group of an adjacent amino acid residue; X is an amine group of an adjacent amino acid residue; and wherein each of $X^1$, $X^2$, $X^3$, $X^4$, $X^5$, and $X^6$ is either unsubstituted or substituted by a conjugate moiety. Optionally, $X^1$, $X^3$ and $X^5$ are each independently an amino acid residue having a D-configuration, or $X^7$; $X^2$, $X^4$ and $X^6$ are each independently an amino acid residue having an L-configuration or $X^1$; and one of $X^1$, $X^2$, $X^3$, $X^4$, $X^5$, and $X^6$ is defined as $X^7$; and each of $X^1$, $X^2$, $X^3$, $X^4$, $X^5$, and $X^6$ is either unsubstituted or substituted by a conjugate moiety. Optionally, $X^1$, $X^3$ and $X^5$ are each independently an amino acid residue having an L-configuration, or $X^7$; $X^2$, $X^4$ and $X^6$ are each independently an amino acid residue having a D-configuration or $X^7$; one of $X^1$, $X^2$, $X^3$, $X^4$, $X^5$, and $X^6$ is defined as $X^7$; and each of $X^1$, $X^2$, $X^3$, $X^4$, $X^5$, and $X^6$ is either unsubstituted or substituted by a conjugate moiety. Optionally, $X^1$ is a D-Leu, D-Nle, D-tert-leucine, D-Ile residue or $X^7$; $X^2$ is a L-Nle, L-Leu, L-tert-leucine, L-Ile residue or $X^7$; $X^3$ is a D-Trp, D-Phe, D-Nal residue or $X^7$; $X^4$ is a L-His, L-Asn residue or $X^7$; $X^5$ is a D-Ser, D-Hse residue or $X^7$; and $X^6$ is a L-Lys, L-Orn, L-Arg residue or $X^7$; and one of $X^1$, $X^2$, $X^3$, $X^4$, $X^5$, and $X^6$ is defined as $X^1$; and each of $X^1$, $X^2$, $X^3$, $X^4$, $X^5$, and $X^6$ is either unsubstituted or substituted by a conjugate moiety. Optionally, the cyclic peptide mimetic has a structure selected from the group consisting of: c(D-Leu-L-Nle-D-Trp-L-His-D-Ser-$X^7$); c(D-Leu-L-Nle-D-Trp-L-His-$X^7$-L-Lys); c(D-Leu-L-Nle-D-Trp-$X^7$-D-Ser-L-Lys); c(D-Leu-L-Nle-$X^7$-L-His-D-Ser-L-Lys); c(D-Leu-$X^7$-D-Trp-L-His-D-Ser-L-Lys); c($X^7$-L-Nle-D-Trp-L-His-D-Ser-L-Lys); and c(D-Leu-L-Nle-D-Trp-D-His-$X^7$-L-Lys) and each of $X^1$, $X^2$, $X^3$, $X^4$, $X^5$, and $X^6$ is either unsubstituted or substituted by a conjugate moiety. Optionally, the cyclic peptide mimetic has a structure selected from the group consisting of: c(D-Leu-L-Nle-D-Trp-L-His-D-Ser-Gly*); c(D-Leu-L-Nle-D-Trp-L-His-Gly*-L-Lys) c(D-Leu-L-Nle-D-Trp-Gly*-D-Ser-L-Lys); c(D-Leu-L-Nle-Gly*-L-His-D-Ser-L-Lys); c(D-Leu-Gly*-D-Trp-L-His-D-Ser-L-Lys); c(Gly*-L-Nle-D-Trp-L-His-D-Ser-L-Lys); c(D-Leu-L-Nle-D-Trp-L-His-D-Ser-Lys*); c(D-Leu-L-Nle-D-Trp-L-His-Hse*-L-Lys); c(D-Leu-L-Nle-D-Trp-L-His-IPrTyr*-L-Lys); c(D-Leu-L-Nle-D-Trp-D-His-IPrTyr*-L-Lys); c(D-Leu-L-Nle-D-Trp-Phe*-D-Ser-L-Lys); c(D-Leu-L-Nle-D-Trp-Tal*-D-Ser-L-Lys); c(D-Leu-L-Nle-D-Trp-Pra*-D-Ser-L-Lys); c(D-Leu-L-Nle-Itr*-L-His-D-Ser-L-Lys); c(D-Leu-Nle*-D-Trp-L-His-D-Ser-L-Lys); c(D-Leu-Phe*-D-Trp-L-His-D-Ser-L-Lys); c(Leu*-L-Nlc-D-Trp-L-His-D-Ser-L-Lys); c(Phe*-L-Nle-D-Trp-L-His-D-Ser-L-Lys); c(4-Phe*-L-Nlc-D-Trp-L-His-D-Ser-L-Lys) and c(D-Leu-L-Nle-D-Trp-L-His-Gly^-L-Lys), wherein an asterisk next to the amino acid code indicates that it is an aza-amino acid residue, having an R group corresponding to the specified amino acid residue, and a caret next to the amino acid code indicates that it is an azasulfuryl-amino acid residue having an R group corresponding to the specified amino acid residue, and wherein Nle is norleucine; Hse is homoserine, Tal is triazole-3-alanine, Itr is isotryptophan, IPrTyr is O-isopropyl-tyrosine, Pra is propargyl glycine and 4F-Phe is 4-fluoro phenylalanine; and wherein each of $X^1$, $X^2$, $X^3$, $X^4$, $X^5$, and $X^6$ is either unsubstituted or substituted by a conjugate moiety. Optionally, one of $X^1$, $X^2$, $X^3$, $X^4$, $X^5$, and $X^6$ is substituted by a conjugate moiety selected from the group consisting of: a protein, a peptide, a nanoparticle, a chelating moiety, a liposome, or a polymer. Optionally, the conjugate moiety is a chelating moiety selected from the group consisting of: NOTA (2-[4,7-bis(carboxymethyl)-1,4,7-triazonan-1-yl] acetic acid) or its derivatives; DOTA (2-[4,7,10-tris(carboxymethyl)-1,4,7,10-tetrazacyclododec-1-yl]acetic acid) or its derivatives; methylhydroxamates derived from triaza- and tetraazamacrocycles ($NOTHA_2$ and $DOTHA_2$) or its derivatives; 1,4,7-triazacyclononane-1-glutaric acid-4,7-diacetic acid (NODAGA) or its derivatives; diethylenetriaminepentaacetate (DTPA) or its derivatives; 1,4,7,10-tetraazadodecane-1,4,7-triacetato (D03A) and its derivatives; 3,6,9,15-tetraazabicyclo[9.3.1]pentadeca-1 (1 5), 11,13-triene-3,6,9-triacetic acid) (PCTA) or its derivatives; 1,4,7,10-tetraazacyclotridecanetetraacetic acid (TRITA) and its derivatives; 1,4,8,11-tetraazacyclotetradecane-1,4,8,11-tetraacetic acid (TETA) and its derivatives; 1,4,7,10-tetraazadodecanetetramethylacetate (DOTMA) and its derivatives; 1,4,7,10-tetraazadodecane-1,4,7-trimethylacetate (D03MA) and its derivatives; N,N',N",N'"-tetraphosphonatomethyl-1,4,7,10-tetraazacyclododecane (DOTP) and its derivatives; 1,4,7,10-tetraazacyclododecane-1,4,7,10-tetrakis(methylene methylphosphonic acid) (DOTMP) and its derivatives; 1,4,7,10-tetraazacyclododecane-1,4,7,10-tetrakis(methylene phenylphosphonic acid) (DOTPP) and its derivatives; or N,N'-ethylenedi-L-cysteine or its derivatives; and N1,N1'-(butane-1,4-diyl)bis(N4-hydroxy-N1-(3-(4-(hydroxy(methyl)amino)-4-oxobutanamido)propyl)-N4-methylsuccinamide) (4HSM) or its derivatives. Optionally, the conjugate moiety is a polyethylene glycol. Optionally, the conjugate moiety is a fluorescent probe. Optionally, the conjugate moiety is bound to an amine group of an R group of an amino acid residue. Optionally, each one of $X^1$, $X^2$, $X^3$, $X^4$, $X^5$, and $X^6$ is unsubstituted by a conjugate moiety.

According to an embodiment, described herein is a conjugate comprising a peptide mimetic and at least one nanoparticle or at least one radioactive metal. Optionally, the radioactive metal is selected from the group consisting of: Copper-64, Copper-67, Gallium-67, Gallium-68, Antimony-117, Antimony-119, Scandium-43, Scandium-44, Scandium-47, Titanium-45, Indium-111, Samarium-153, Strontium-89, Yttrium-90, Lutetium-177, Bismuth-213 and Actinium-225.

According to an embodiment, described herein is a method for treatment of an amyloidogenic disease in a patient in need thereof comprising administering to the patient a cyclic peptide mimetic or a conjugate as described herein. Optionally, the patient suffers from a disease selected from the group consisting of: Alzheimer's disease, Parkinson's disease, or Huntington's Disease. Optionally, the disease is a prion disease, systemic amyloidosis, cataract, and ALS.

According to an embodiment, described herein is a method for imaging a subject comprising administering to the subject a cyclic peptide mimetic or a conjugate described herein and performing on the subject positron emission computed tomography (PET); single-photon emission computed tomography (SPECT), CT, or magnetic resonance imaging (MRI). According to an embodiment, described herein is a method for early imaging of a amyloid beta in a subject suspected of amyloidogenic pathology comprising administering to the subject a cyclic peptide mimetic or a conjugate described herein, and performing on the subject positron emission computed tomography (PET); single-photon emission computed tomography (SPECT), CT, or magnetic resonance imaging (MRI).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A cyclic peptide mimetic having the structure c ($X^1$-$X^2$-$X^3$-$X^4$-$X^5$-$X^6$) wherein:

each of $X^1$, $X^2$, $X^3$, $X^4$, $X^5$, and $X^6$ is either an L-amino acid residue, a D-amino acid residue, or $X^7$; and wherein one of $X^1$, $X^2$, $X^3$, $X^4$, $X^5$, and $X^6$ is defined as $X^7$; and wherein the remaining $X^1$, $X^2$, $X^3$, $X^4$, $X^5$, and $X^6$ which are not defined as $X^7$ are amino acid residues in alternating L-configuration and D-configuration;

wherein $X^7$ is an aza-amino acid residue or azasulfuryl-amino acid residue having the structure:

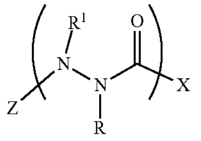

or

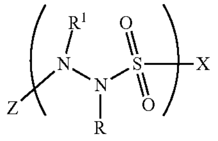

wherein the R group is the same R group as defined in naturally occurring and synthetic amino acids; $R^1$ is hydrogen, alkyl, aryl, heteroalkyl, heteroaryl, aryl alkyl or heteroaryl alkyl, or $R^1$ and R could together form a cyclic ring; Z is a carbonyl group of an adjacent amino acid residue; X is an amine group of an adjacent amino acid residue;

and wherein each of $X^1$, $X^2$, $X^3$, $X^4$, $X^5$, and $X^6$ is either unsubstituted or substituted by a conjugate moiety.

2. The cyclic peptide mimetic according to claim 1, wherein:

$X^1$, $X^3$ and $X^5$ are each independently an amino acid residue having a D-configuration, or $X^7$;

$X^2$, $X^4$ and $X^6$ are each independently an amino acid residue having an L-configuration or $X^7$;

and wherein one of $X^1$, $X^2$, $X^3$, $X^4$, $X^5$, and $X^6$ is defined as $X^7$;

and wherein each of $X^1$, $X^2$, $X^3$, $X^4$, $X^5$, and $X^6$ is either unsubstituted or substituted by a conjugate moiety.

3. The cyclic peptide mimetic according to claim 1, wherein:

$X^1$, $X^3$ and $X^5$ are each independently an amino acid residue having an L-configuration, or $X^1$;

$X^2$, $X^4$ and $X^6$ are each independently an amino acid residue having a D-configuration or $X^7$;

and wherein one of $X^1$, $X^2$, $X^3$, $X^4$, $X^5$, and $X^6$ is defined as $X^1$;

and wherein each of $X^1$, $X^2$, $X^3$, $X^4$, $X^5$, and $X^6$ is either unsubstituted or substituted by a conjugate moiety.

4. The cyclic peptide mimetic according to claim 3 wherein:

$X^1$ is a D-Leu, D-Nle, D-tert-leucine, D-Ile residue or $X^7$;

$X^2$ is a L-Nle, L-Leu, L-tert-leucine, L-Ile residue or $X^7$;

$X^3$ is a D-Trp, D-Phe, D-Nal residue or $X^7$;

$X^4$ is a L-His, L-Asn residue or $X^7$;

$X^5$ is a D-Ser, D-Hse residue or $X^7$; and $X^6$ is a L-Lys, L-Orn, L-Arg residue or $X^7$;

and wherein one of $X^1$, $X^2$, $X^3$, $X^4$, $X^5$, and $X^6$ is defined as $X^7$;

and wherein each of $X^1$, $X^2$, $X^3$, $X^4$, $X^5$, and $X^6$ is either unsubstituted or substituted by a conjugate moiety.

5. The cyclic peptide mimetic according to claim 1, having a structure selected from the group consisting of:

c(D-Leu-L-Nle-D-Trp-L-His-D-Ser-$X^7$)

c(D-Leu-L-Nle-D-Trp-L-His-$X^7$-L-Lys)

c(D-Leu-L-Nle-D-Trp-$X^7$-D-Ser-L-Lys)

c(D-Leu-L-Nle-$X^7$-L-His-D-Ser-L-Lys)

c(D-Leu-$X^7$-D-Trp-L-His-D-Ser-L-Lys)

-continued c($X^7$-L-Nle-D-Trp-L-His-D-Ser-L-Lys);
and c(D-Leu-L-Nle-D-Trp-D-His-$X^7$-L-Lys)

and wherein each of $X^1$, $X^2$, $X^3$, $X^4$, $X^5$, and $X^6$ is either unsubstituted or substituted by a conjugate moiety.

6. The cyclic peptide mimetic according to claim 1, having a structure selected from the group consisting of:

c(D-Leu-L-Nle-D-Trp-L-His-D-Ser-Gly*)

c(D-Leu-L-Nle-D-Trp-L-His-Gly*-L-Lys)

c(D-Leu-L-Nle-D-Trp-Gly*-D-Ser-L-Lys)

c(D-Leu-L-Nle-Gly*-L-His-D-Ser-L-Lys)

c(D-Leu-Gly*-D-Trp-L-His-D-Ser-L-Lys)

c(Gly*-L-Nle-D-Trp-L-His-D-Ser-L-Lys)

c(D-Leu-L-Nle-D-Trp-L-His-D-Ser-Lys*)

c(D-Leu-L-Nle-D-Trp-L-His-Hse*-L-Lys)

c(D-Leu-L-Nle-D-Trp-L-His-IPrTyr*-L-Lys)

c(D-Leu-L-Nle-D-Trp-D-His-IPrTyr*-L-Lys)

c(D-Leu-L-Nle-D-Trp-Phe*-D-Ser-L-Lys)

c(D-Leu-L-Nle-D-Trp-Tal*-D-Ser-L-Lys)

c(D-Leu-L-Nle-D-Trp-Pra*-D-Ser-L-Lys)

c(D-Leu-L-Nle-Itr*-L-His-D-Ser-L-Lys)

c(D-Leu-Nle*-D-Trp-L-His-D-Ser-L-Lys)

c(D-Leu-Phe*-D-Trp-L-His-D-Ser-L-Lys)

c(Leu*-L-Nle-D-Trp-L-His-D-Ser-L-Lys)

c(Phe*-L-Nle-D-Trp-L-His-D-Ser-L-Lys)

c(4-Phe*-L-Nle-D-Trp-L-His-D-Ser-L-Lys)
and c(D-Leu-L-Nle-D-Trp-L-His-Gly^-L-Lys), wherein an asterisk next to the amino acid code indicates that it is an aza-amino acid residue, having an R group corresponding to the specified amino acid residue, and a caret next to the amino acid code indicates that it is an azasulfuryl-amino acid residue having an R group corresponding to the specified amino acid residue, and wherein Nle is norleucine; Hse is homoserine, Tal is triazole-3-alanine, Itr is isotryptophan, IPrTyr is O-isopropyl-tyrosine, Pra is propargyl glycine and 4F-Phe is 4-fluoro phenylalanine;

and wherein each of $X^1$, $X^2$, $X^3$, $X^4$, $X^5$, and $X^6$ is either unsubstituted or substituted by a conjugate moiety.

7. The cyclic peptide mimetic according to claim 1 wherein one of $X^1$, $X^2$, $X^3$, $X^4$, $X^5$, and $X^6$ is substituted by a conjugate moiety selected from the group consisting of: a protein, a peptide, a nanoparticle, a chelating moiety, a liposome, or a polymer.

8. The cyclic peptide according to claim 7 wherein the conjugate moiety is a chelating moiety selected from the group consisting of: NOTA (2-[4,7-bis(carboxymethyl)-1,4,7-triazonan-1-yl]acetic acid) or its derivatives; DOTA (2-[4,7,10-tris(carboxymethyl)-1,4,7,10-tetrazacyclododec-1-yl]

acetic acid) or its derivatives; methylhydroxamates derived from triaza- and tetraazamacrocycles ($NOTHA_2$ and $DOTHA_2$) or its derivatives; 1,4,7-triazacyclononane-1-glutaric acid-4,7-diacetic acid (NODAGA) or its derivatives; diethylenetriaminepentaacetate (DTPA) or its derivatives; 1,4,7,10-tetraazadodecane-1,4,7-triacetate (D03A) and its derivatives; 3,6,9,15-tetraazabicyclo[9.3.1]pentadeca-1(15),11,13-triene-3,6,9-triacetic acid) (PCTA) or its derivatives; 1,4,7,10-tetraazacyclotridecanetetraacetic acid (TRITA) and its derivatives; 1,4,8,11-tetraazacyclotetradecane-1,4,8,11-tetraacetic acid (TETA) and its derivatives; 1,4,7,10-tetraazadodecanetetramethylacetate (DOTMA) and its derivatives; 1,4,7,10-tetraazadodecane-1,4,7-trimethylacetate (D03MA) and its derivatives; N,N',N'',N'''-tetraphosphonatomethyl-1,4,7,10-tetraazacyclododecane (DOTP) and its derivatives; 1,4,7,10-tetraazacyclododecane-1,4,7,10-tetrakis(methylene methylphosphonic acid) (DOTMP) and its derivatives; 1,4,7,10-tetraazacyclododecane-1,4,7,10-tetrakis(methylene phenylphosphonic acid) (DOTPP) and its derivatives; or N,N'-ethylenedi-L-cysteine or its derivatives; and N1,N1'-(butane-1,4-diyl)bis(N4-hydroxy-N1-(3-(4-(hydroxy(methyl)amino)-4-oxobutanamido) propyl)-N4-methylsuccinamide) (4HSM) or its derivatives.

9. The cyclic peptide mimetic according to claim 7 wherein the conjugate moiety is a polyethylene glycol.

10. The cyclic peptide mimetic according to claim 7 wherein the conjugate moiety is a fluorescent probe.

11. The cyclic peptide mimetic according to claim 7 wherein the conjugate moiety is bound to an amine group of an R group of an amino acid residue.

12. The cyclic peptide mimetic according to claim 1 wherein each one of $X^1$, $X^2$, $X^3$, $X^4$, $X^5$, and $X^6$ is unsubstituted by a conjugate moiety.

13. A conjugate comprising a peptide mimetic according to claim 1 and at least one nanoparticle or at least one radioactive metal.

14. The conjugate according to claim 13 wherein the radioactive metal is selected from the group consisting of: Copper-64, Copper-67, Gallium-67, Gallium-68, Antimony-117, Antimony-119, Scandium-43, Scandium-44, Scandium-47, Titanium-45, Indium-111, Samarium-153, Strontium-89, Yttrium-90, Lutetium-177, Bismuth-213 and Actinium-225.

15. A method for treatment of an amyloidogenic disease in a patient in need thereof comprising administering to the patient a cyclic peptide mimetic according to claim 1 or a conjugate comprising the cyclic peptide mimetic.

16. The method according to claim 15 wherein the patient suffers from a disease selected from the group consisting of: Alzheimer's disease, Parkinson's disease, Huntington's Disease, a prion disease, systemic amyloidosis, cataract, and ALS.

17. A method for imaging a subject comprising administering to the subject a cyclic peptide mimetic according to claim 1 or a conjugate comprising it, and performing on the subject positron emission computed tomography (PET); single-photon emission computed tomography (SPECT), CT, or magnetic resonance imaging (MRI).

18. A method for early imaging of an amyloid beta in a subject suspected of amyloidogenic pathology comprising administering to the subject a cyclic peptide mimetic according to claim 1 or a conjugate comprising it, and performing on the subject positron emission computed tomography (PET); single-photon emission computed tomography (SPECT), CT, or magnetic resonance imaging (MRI).

* * * * *